United States Patent [19]

Lacroix et al.

[11] Patent Number: 5,359,029

[45] Date of Patent: Oct. 25, 1994

[54] PEPTIDES AND ANALOGUES AND MIXTURES THEREOF FOR DETECTING ANTIBODIES TO HTLV-I AND HTLV-II VIRUSES

[75] Inventors: Martial Lacroix, Brossard; Maan Zrein, Laval, both of Canada

[73] Assignee: Biochem Immunosystems Inc., Montreal, Canada

[21] Appl. No.: 672,483

[22] Filed: Mar. 20, 1991

Related U.S. Application Data

[63] Continuation-in-part of Ser. No. 554,258, Jul. 18, 1990, abandoned.

[51] Int. Cl.$^5$ .................. C07K 7/00; C07K 7/10; G01N 33/569
[52] U.S. Cl. .................. 530/300; 530/324; 530/325; 530/326; 530/403; 530/826; 435/5
[58] Field of Search .............. 435/5; 424/89; 530/300, 530/826

[56] References Cited

U.S. PATENT DOCUMENTS 4,525,300 6/1985 Yoshida et al. .................. 530/237
4,629,783 12/1986 Cosand .................. 530/325
5,066,579 11/1991 Reyes .................. 530/324

FOREIGN PATENT DOCUMENTS 0267622 5/1988 European Pat. Off. .

OTHER PUBLICATIONS

Gnann et al, Science 237: 1346-1349, 1987.
Shimotohno et al, PNAS 82, 1985, pp. 3101-3105.
Seiki et al, PNAS 82, 1983, pp. 3618-3622.
Harlow et al, "Antibodies A Laboratory Manual" 1988 Cold Spring Harbor, N.Y. pp. 72-77, 86, 87.
Hilleman, "Human Retroviruses, Cancer and AIDS"Ed. Dani Bolognesi:, Alan R. Liss, N.Y. pp. 302-303, 1988.
Bell et al "Progress Towards Better Vaccines" Oxford Press, N.Y. 1986, pp. 77-88.
Palker et al. J. Immunol 136(7) 1986, pp. 2393-2397.
Takehara et al., Int J. Cancer 44. 1989 pp. 332-336.
Palker et al, J. Immunol. 142(3) 1989, pp. 971-978.
Palker et al, J. Immunol 135(1) 1985, pp. 247-254.
Sodrowski et al, Science 225, 1984, pp. 421-424.
Peltola et al, The Lancet Apr. 26, 1986, pp. 939-942.

*Primary Examiner*—Christine M. Nucker
*Assistant Examiner*—Chris Dubrule
*Attorney, Agent, or Firm*—Nixon & Vanderhye

[57] ABSTRACT

This invention relates to novel linear peptides and mixtures and chemical combinations thereof useful for detecting and quantifying HTLV-I and HTLV-II infections. These peptides are also useful in vaccines against HTLV-I and HTLV-II vital infections.

13 Claims, 2 Drawing Sheets

```
HTLV-1    1   MGKFLATLILFFQFCPLIFGDYSPSCCTLTIGVSSYHSKPCNPAQPVCSW
HTLV-II   1   MGNFV..FLLLFSLTHFPLAQ..QSRCTLTIGISSYHSSPCSPTQPVCTW

51   TLDLLALSADQALQPPCPNLVSYSSYHATYSLYLFPHWTKKPNRNGGGYY
         47   NLDLNSLTTDQRLHPPCPNLITYSGFHKTYSLYLFPHWIKKPNRQGLGYY

101   SASYSDPCSLKCPYLGCQSWTCPYTGAVSSPYWKFQHDVNFTQEVSRLNI
         97   SPSYNDPCSLQCPYLGCQAWTSAYTGPVSSPSWKFHSDVNFTQEVSQVSL

151   NLHFSKCGFPFSLLVDAPGYDPIWFLNTEPSQLPPTAPPLLPHSNLDHIL
        147   RLHFSKCGSSMTLLVDAPGYDPLWFITSEPTQPPPTSPPLVHDSDLEHVL

201   EPSIPWKSKLLTLVQLTLQSTNYTCIVCIDRASLSTWHVLYSPNVSVP.S
        197   TPSTSWTTKILKFIQLTLQSTNYSCMVCVDRSSLSSWHVLYTPNISIPQQ

250   SSSTPLLYPSLALPAPHLTLPFNWTHCFDPQIQAIVSSPCHNSLILPPFS
        247   TSSRTILFPSLALPAPP.SQPFPWTHCYQPRLQAITTDNCNNSIILPPFS gp46<>gp21
        300   LSPVPTLGSRSRRAVPVAVWLVSALAMGAGVAGGITGSMSLASGKSLLHE
        296   LAPVPPPATRRRRAVPIAVWLVSALAAGTGIAGGVTGSLSLASSKSLLLE
                gp46<>gp21

350   VDKDISQLTQAIVKNHKNLLKIAQYAAQNRRGLDLLFWEQGGLCKALQEQ
        346   VDKDISHLTQAIVKNHQNILRVAQYAAQNRRGLDLLFWEQGGLCKAIQEQ

400   CRFPNITNSHVPILQERPPLENRVLTGWGLNWDLGLSQWAREALQTGITL
        396   CCFLNISNTHVSVLQERPPLEKRVITGWGLNWDLGLSQWAREALQTGITI

450   VALLLLVILAGPCILRQLRHLPSRV..RYPHYSLIKPESSL
        446   LALLLLVILFGPCILRQIQALPQRLQNRHNQYSLINPETML
```

Fig. 1

```
HTLV-1     1  MGKFLATLILFFQFCPLIFGDYSPSCCTLTIGVSSYHSKPCNPAQPVCSW
HTLV-II    1  MGNFV..FLLLFSLTHFPLAQ..QSRCTLTIGISSYHSSPCSPTQPVCTW

51  TLDLLALSADQALQPPCPNLVSYSSYHATYSLYLFPHWTKKPNRNGGGYY
          47  NLDLNSLTTDQRLHPPCPNLITYSGFHKTYSLYLFPHWIKKPNRQGLGYY

101  SASYSDPCSLKCPYLGCQSWTCPYTGAVSSPYWKFQHDVNFTQEVSRLNI
          97  SPSYNDPCSLQCPYLGCQAWTSAYTGPVSSPSWKFHSDVNFTQEVSQVSL

151  NLHFSKCGFPFSLLVDAPGYDPIWFLNTEPSQLPPTAPPLLPHSNLDHIL
         147  RLHFSKCGSSMTLLVDAPGYDPLWFITSEPTQPPPTSPPLVHDSDLEHVL

201  EPSIPWKSKLLTLVQLTLQSTNYTCIVCIDRASLSTWHVLYSPNVSVP.S
         197  TPSTSWTTKILKFIQLTLQSTNYSCMVCVDRSSLSSWHVLYTPNISIPQQ

250  SSSTPLLYPSLALPAPHLTLPFNWTHCFDPQIQAIVSSPCHNSLILPPFS
         247  TSSRTILFPSLALPAPP.SQPFPWTHCYQPRLQAITTDNCNNSIILPPFS
                   gp46<>gp21
         300  LSPVPTLGSRSRRAVPVAVWLVSALAMGAGVAGGITGSMSLASGKSLLHE
         296  LAPVPPPATRRRRAVPIAVWLVSALAAGTGIAGGVTGSLSLASSKSLLLE
                   gp46<>gp21
         350  VDKDISQLTQAIVKNHKNLLKIAQYAAQNRRGLDLLFWEQGGLCKALQEQ
         346  VDKDISHLTQAIVKNHQNILRVAQYAAQNRRGLDLLFWEQGGLCKAIQEQ

400  CRFPNITNSHVPILQERPPLENRVLTGWGLNWDLGLSQWAREALQTGITL
         396  CCFLNISNTHVSVLQERPPLEKRVITGWGLNWDLGLSQWAREALQTGITI

450  VALLLLVILAGPCILRQLRHLPSRV..RYPHYSLIKPESSL
         446  LALLLLVILFGPCILRQIQALPQRLQNRHNQYSLINPETML
```

Fig. 2

```
HTLV-1    1   MGQIFSRSASPIPRPPRGLAAHHWLNFLQAAYRLEPGPSSYDFHQLKKFL
HTLV-II   1   MGQIHGLSPTPIPKAPRGLSTHHWLNFLQAAYRLQPRPSDFDFQQLRRFL

51  KIALETPARICPINYSLLASLLPKGYPGRVNEILHILIQTQAQIPSRPA?
          51  KLALKTPIWLNPIDYSLLASLIPKGYPGRVVEIINILVKNQVSPSAPAAP p19 <> p24
          101 ......PPPSSPTHDPPDSDPQIPPPYVEPTAPQVLPVMHPHGAPPNHRP
          101 VPTPICPTTTPPPPPPPSPEAHVPPPYVEPTTTQCFPILHPPGAPSAHRP
                                                  p15 <> p24

145 WQMKDLQAIKQEVSQAAPGSPQFMQTIRLAVQQFDPTAKDLQDLLQYLCS
          151 WQMKDLQAIKQEVSSSALGSPQFMQTLRLAVQQFDPTAKDLQDLLQYLCS

195 SLVASLHHQQLDSLISEAETRGITGYNPLAGPLRVQANNPQQQGLRREYQ
          201 SLVVSLHHQQLNTLITEAETRGMTGYNPMAGPLRMQANNPAQQGLRREYQ

245 QLWLAAFAALPGSAKDPSWASILQGLEEPYHAFVERLNIALDNGLPEGTP
          251 NLWLAAFSTLPGNTRDPSWAAILQGLEEPYCAFVERLNVALDNGLPEGTP

295 KDPILRSLAYSNANKECQKLLQARGHTNSPLGDMLRACQTWTPKDKTKVL
          301 KEPILRSLAYSNANKECQKILQARGHTNSPLGEMLRTCQAWTPKDKTKVL

> p15
          345 VVQPKKPPPNQPCFRCGKAGHWSRDCTQPRPPPGPCPLCQDPTHWKRDCP
          351 VVQPRRPPPTQPCFRCGKVGHWSRDCTQPRPPPGPCPLCQDPSHWKRDCP
                > p12

395 RLKPTIPEPEPEEDALLLDLP..ADIPHPKNSIGGEV
          401 QLKP....PQEEGEPLLLDLPSTSGTTEEKNSLRGEI
```

PEPTIDES AND ANALOGUES AND MIXTURES THEREOF FOR DETECTING ANTIBODIES TO HTLV-I AND HTLV-II VIRUSES

This application is a continuation-in-part of U.S. patent application Ser. No. 07/554,258 filed Jul. 18, 1990, abandoned.

TECHNICAL FIELD OF THE INVENTION

This invention relates to novel linear peptides and mixtures and chemical combinations thereof useful for detecting and quantifying HTLV-I and HTLV-II infections. These peptides are also useful in vaccines against HTLV-I and HTLV-II viral infections.

BACKGROUND OF THE INVENTION

Human T-cell leukemia virus subgroup I (HTLV-I) is a retrovirus closely associated with adult T-cell leukemia/lymphoma (ATL) (Poiesz et al., 1980, Proc. Natl. Acad. Sci. U.S.A., 77, 7415–7419). It is also linked with neurological diseases designated as tropical spastic paraparesis and HTLV-I-associated myelopathy (HAM) (Gessain et al., 1985, Lancet ii, 407–410). Human T-cell leukemia virus subgroup II (HTLV-II) was first isolated from a patient with T-cell hairy cell leukemia (Kalyanaraman et al., 1982, Science, 218, 571–573). It is associated with a T-cell variant of hairy cell leukemia.

The HTLV-I and HTLV-II genomes exist as proviruses in the human chromosomal DNA of leukemia cells. Their complete nucleotide sequences have been elucidated (Seiki et al., 1983, Proc. Natl. Acad. Sci. U.S.A., 80, 3618–3622; Shimotohno et al., 1985, Ibid., 82, 3101–3105). Like other retroviruses, the HTLV-I and HTLV-II genomes are flanked by LTR (long-terminal-repeats) structures which are believed to play an essential role in the integration of the proviral DNA into the host chromosomal DNA. Four major genes have been identified and occupy the following relative positions in the genome: LTR-gag-pol-env-pX-LTR (Seiki et al.; Shaw et al., 1984, Proc. Natl. Acad. Sci., 81, 4544–4548). The gag gene codes for a 48,000-dalton-precursor protein (often referred to as p53) consisting of 429 amino acids (433 for HTLV-II). This precursor protein is cleaved into at least three smaller proteins (FIG. 2). The pol gene codes for the viral reverse transcriptase. The env gene presumably codes for a 54,000-dalton protein which is glycosylated and later cleaved into two glycoproteins named gp46 and gp21. (Slightly different molecular weights have been reported for what are most probably the same env gene protein products). The last coding region is called pX and is believed to code for four proteins ($tax_1$, $tax_2$, $rex_1$, $rex_2$) involved in gene expression and regulation.

As depicted in FIGS. 1 and 2, the env proteins and the gag proteins of HTLV-I and of HTLV-II share a high degree of amino acid sequence homology. Furthermore, serologic cross-reactivity has been reported between the proteins of HTLV-I and those of HTLV-II (Lee et al., 1984, Proc. Natl. Acad. Sci., 81, 7579–7583). Despite this structural resemblance and cross-reactivity, some regions of these env and gag proteins are recognized only by antibodies present in a patient infected by either the HTLV-I or the HTLV-II virus.

HTLV-I and HTLV-II both differ from the human immunodeficiency viruses (HIVs) in their morphologic and genetic structures. As a result, antibodies to the HIV proteins should not cross-react with HTLV-I and HTLV-II antigens. However, some serum samples taken from patients with AIDS have shown some degree of cross-reactivity with HTLV antigens (Essex et al., 1983, Science, 220, 859–862).

Adult T-cell leukemia/lymphoma (ATL) occurs mainly in Southwestern Japan, the Caribbean basin and parts of Central and South America. In those regions, seroprevalence varies between 5% and 15% in the general population and reaches 30% in older age groups. In the United States, HTLV-I/II infections are mainly present in intravenous drug users (IVDU). In a recent American Red Cross survey (Williams et al., 1988, Science, 240, 643–646), antibodies to HTLV-I could be detected in 10 of 39,898 random blood donors in eight U.S. cities; this represents a seroprevalence rate of 0.025%. A similar study involving 3158 individuals from Northern Egypt led to the identification of two carriers (prevalence rate of 0.06%) (El-Farrash et al., 1988, Microbiol. Immunol., 32, 981–984). In these two studies, distinction between infection with HTLV-I and HTLV-II was not clearly established. These data indicate that there is a need for a reliable test to screen all blood samples destined for blood banks in order to avoid the inadvertent spread of the virus to blood product recipients.

There have been several attempts in the prior art to develop such tests. None has been successful in detecting all serum and plasma samples that are part of a well characterized commercial panel of HTLV infected fluids. Furthermore, none is able to detect HTLV infection at very low levels, thereby, ensuring safety of the blood supply and prompt and early treatment of HTLV infections.

Saxinger et al. (1984, Science, 225, 1473–1476) has reported the use of the HTLV-I particle as the immunoadsorbent in an enzyme immunoassay (EIA) for the detection of antibodies to the virus. In an improvement to this first generation test, specific HTLV antigens have been used instead of viral particles as the immunoadsorbent. For example, Samuel et al. (1984, Science, 225, 1094–1097) refers to antigens obtained by recombinant DNA technology. These detected each of 11 sera shown to contain antibodies to HTLV-I by a whole viral lysate-based EIA similar to the one developed by Saxinger et al. Slamon et al. (PCT/US85/01803) refer to assays using polypeptides and fragments thereof associated with immunogenic sites present on proteins of the pX region of HTLV-1 and HTLV-II. The reported accuracy of these assays ranged between 77% and 87%. Fukui et al. (European Patent Application 87116787) refers to assays using polypeptides encoded by a fused gene comprising all or a part of the gag gene and all or a part of the env gene. They reported a sensitivity of 100% (57/57) with no false-positives.

Although these results look impressive, they are likely not repeatable with sera, like those most usual in the United States, which are characterized by much lower antibody titers than the Japanese sera used to validate the above assays.

Assays which use peptides derived from HTLV-I or HTLV-II proteins have also been reported. For example, Palker et al. (1989, J. Immunol., 142, 971–978) reports that antibodies in sera from 28 out of 36 patients (78%) reacted with a peptide spanning amino acids 190 to 209 of the HTLV-I envelope (peptide 4a; env 190–209).* Ten of 35 sera samples (29%) reacted with peptide 6 (env 296–312) and 6 out of 33 (18%) bound to peptide 7 (env 374–392). Palker et al. (1986, J. Immunol., 136, 2393–2397) also refers to a peptide (SP-71; gag 120–130) that reacted with 16 out of 18 HTLV-I seropositive samples.

*In this application, the amino acid sequence and numbering published by Seiki et al. (supra.) and by Shimotohno et al. (supra.) for the HTLV-I and HTLV-II gene products are used (for ease of reference only).

A peptide (SP-70; env 296–306) has been reported by Copeland et al. (1986, J. Immunol., 137, 2945–2951) to recognize antibodies from 4 out of 12 individuals seropositive for HTLV-I.

Wang et al. (U.S. Pat. No. 4,833,071) refers to three overlapping linear peptides spanning regions of the transmembrane protein (gp21) of HTLV-I. These peptides (env 381–400, env 377–400 and env 378–393), when used in a mixture, detected 102 out of 102 serum samples from patients with ATL and 5 out of 30 patients with AIDS/ARC. No immunoreactivity was found against sera from 12 normal subjects or from 12 patients with autoimmune diseases.

Reyes (PCT/WO89/06543) refers to a non-glycosylated, 41-amino acid recombinant peptide antigen derived from the gp46 of HTLV-I. This recombinant peptide, env(163–203), is reported to have been used in a solid-phase assay for the determination of serum antibodies in six patients with HTLV-I infection.

Vahlne (PCT/WO89/08664) refers to four synthetic peptides, A, B, C and H, spanning env(381–404), env(2-73–293), env(223–242) and env(176–199) of the envelope protein of HTLV-I. From the examples provided, it appears that only peptide A was useful in an ELISA for the detection of specific antibodies to HTLV-I present in the samples tested.

None of the above-described assays has demonstrated the high specificity (no false positives) and high sensitivity (detection of all positives, even when the sera contains very low levels of HTLV antibodies) necessary to ensure that HTLV infected blood products do not enter blood banks and that infected individuals seek prompt and early treatment. The peptides of this invention remedy these failures.

SUMMARY OF THE INVENTION

The peptides of this invention are selected from the group consisting of:
(i) peptides having the formula:

$$a - X1 - b$$

wherein:
X1 is a sequence of at least six amino acids taken as a block from $AA_{283}-AA_{309}$ (SEQ ID NO:5) of the gp46 env protein (HTLV-I) and analogues thereof;
a is an amino terminus, one to eight amino acids or a substituent effective to facilitate coupling or to improve the immunogenic or antigenic activity of the peptide; and
b is a carboxy terminus, one to eight amino acids or a substituent effective to facilitate coupling or to improve the immunogenic or antigenic activity of the peptide;
(ii) peptides having the formula:

$$a - X2 - b$$

wherein:
X2 is a sequence of at least six amino acids taken as a block from $AA_{273}-AA_{305}$ (SEQ ID NO:18) of the gp46 env protein (HTLV-II), and analogues thereof and a and b are as defined above;
(iii) peptides having the formula:

$$a - Z1 - b$$

wherein:
Z1 is a sequence of at least six amino acids taken as a block from $AA_{236}-AA_{257}$ (SEQ ID NO:13) of the gag p24 protein (HTLV-I), and analogues thereof and a and b are as defined above;
(iv) peptides having the formula:

$$a - Z2 - b$$

wherein:
Z2 is a sequence of at least six amino acids taken as a block from $AA_{242}-AA_{263}$ (SEQ ID NO:14) of the gag p24 protein (HTLV-II), and analogues thereof and a and b are as defined above;
(v) peptides having the formula:

$$a - B2 - b$$

wherein:
B2 is a sequence of at least six amino acids taken as a block from $AA_{171}-AA_{207}$ (SEQ ID NO:19) of the gp46 env protein (HTLV-II), and analogues thereof and a and b are as defined above; and
(vi) tandem peptides having the formula:

$$a-((((J)_n-c)_o-((U)_p)_q-d)_r)_s-b$$

wherein:
J and U are sequences of at least six amino acids taken as a block from sequences independently selected from the group consisting of $AA_{193}-AA_{210}$ (SEQ ID NO:16) or $AA_{283}-AA_{309}$ (SEQ ID NO:5) of the gp46 env protein (HTLV-I); $AA_{236}-AA_{257}$ (SEQ ID NO:15) of the p24 gag protein (HTLV-I); $AA_{120}-AA_{130}$ (SEQ ID NO:17) of the p19 gag protein (HTLV-I); $AA_{171}-AA_{207}$ (SEQ ID NO:19) or $AA_{273}-AA_{305}$ (SEQ ID NO:18) of the gp46 env protein (HTLV-II); $AA_{242}-AA_{263}$ (SEQ ID NO:14) of the p24 gag protein (HTLV-II) and $AA_{126}-AA_{136}$ (SEQ ID NO:20) of the p19 gag protein (HTLV-II); and analogues thereof;
a and b are as defined above;
c and d, if present, are independently selected from one to eight amino acids or a substituent effective to facilitate coupling or to improve the immunogenic or antigenic activity of the peptide;
n=1–5;
o=1–5 if c is present, otherwise o=1;
p=1–5;
q=1–5;
r=1–5 if d is present, otherwise r=1; and
s=1–5.

The peptides and mixtures thereof of this invention are useful for the screening of blood and body fluids for the presence of HTLV-I and HTLV-II infraction and in the preparation of safe, effective vaccines against HTLV-I and HTLV-II infections. For example, the peptides of this invention and mixtures thereof are useful in a wide variety of specific binding assays for the detection of antibodies to HTLV-I and HTLV-II, as immunogens for eliciting antibodies useful for the detection of HTLV-I and HTLV-II antigens and in the preparation of vaccines against HTLV-I and HTLV-II viral infections.

BRIEF DESCRIPTION OF THE DRAWINGS

FIG. 1 depicts the amino acid sequence of the env gene products (gp46 and gp21) of HTLV-I (SEQ ID NO:1) and HTLV-II (SEQ ID NO:2). The amino acid residues of the sequence are given using the following single letter code: A=ala, C=cys, D=asp, E=glu, F=phe, G=gly, H=his, I=ile, K=lys, L=leu, M=met, N=asn, P=pro, Q=gln, R=arg, S=ser, T=thr, V=val, W=trp, Y=tyr. The "..." are spaces added to align the depicted sequences as closely as possible.

FIG. 2 depicts the amino acid sequence of the gag gene products of HTLV-I (SEQ ID NO:3) and HTLV-II (SEQ ID NO:4). Again, the "..." are spaces added to align the depicted sequences as closely as possible.

DESCRIPTION OF THE INVENTION

The present invention provides novel peptides and analogues thereof corresponding to immunodominant regions of the env gene and gag gene products of HTLV-I and HTLV-II. It also provides mixtures and chemical combinations of those peptides and analogues. As will be plain from the following description, these peptides, analogues, mixtures and chemical combinations are useful in a wide variety of diagnostic and preventive methods, means and compositions with respect to HTLV-I and HTLV-II and the infections caused by them. Some of the peptides, analogues, mixtures and chemical combinations of this invention are also capable of distinguishing with which virus, HTLV-I or HTLV-II, a particular patient is infected.

As set forth above, the peptides of this invention are selected from the group consisting of:
(i) peptides having the formula:

$$a-X1-b$$

wherein:
X1 is a sequence of at least six amino acids taken as a block from $AA_{283}$–$AA_{309}$ of the gp46 env protein (HTLV-I), and analogues thereof;
a is an amino terminus, one to eight amino acids or a substituent effective to facilitate coupling or to improve the immunogenic or antigenic activity of the peptide; and
b is a carboxy terminus, one to eight amino acids or a substituent effective to facilitate coupling or to improve the immunogenic or antigenic activity of the peptide;
(ii) peptides having the formula:

$$a-X2-b$$

wherein:
X2 is a sequence of at least six amino acids taken as a block from $AA_{273}$–$AA_{305}$ of the gp46 env protein (HTLV-II), and analogues thereof and a and b are as defined above;
(iii) peptides having the formula:

$$a-Z1-b$$

wherein:
Z1 is a sequence of at least six amino acids taken as a block from $AA_{236}$–$AA_{257}$ of the gag p24 protein (HTLV-I), and analogues thereof and a and b are as defined above;
(iv) peptides having the formula:

$$a-Z2-b$$

wherein:
Z2 is a sequence of at least six amino acids taken as a block from $AA_{242}$–$AA_{263}$ of the gag p24 protein (HTLV-II), and analogues thereof and a and b are as defined above;
(v) peptides having the formula:

$$a-B2-b$$

wherein:
B2 is a sequence of at least six amino acids taken as a block from $AA_{171}$–$AA_{207}$ of the gp46 env protein (HTLV-II), and analogues thereof and a and b are as defined above; and
(vi) tandem peptides having the formula:

$$a-((((J)_n-c)_o-((U)_p)_q-d)_r)_s-b$$

wherein:
J and U are sequences of at least six amino acids taken as a block from sequences independently selected from the group consisting of $AA_{193}$–$AA_{210}$ or $AA_{283}$–$AA_{309}$ of the gp46 env protein (HTLV-I); $AA_{236}$–$AA_{257}$ of the p24 gag protein (HTLV-I); $AA_{120}$–$AA_{130}$ of the p19 gag protein (HTLV-I); $AA_{171}$–$AA_{207}$ or $AA_{273}$–$AA_{305}$ of the gp46 env protein (HTLV-II); $AA_{242}$–$AA_{263}$ of the p24 gag protein (HTLV-II) and $AA_{126}$–$AA_{136}$ of the p19 gag protein (HTLV-II); and analogues thereof;
a and b are as defined above;
c and d, if present, are independently selected from one to eight amino acids or a substituent effective to facilitate coupling or to improve the immunogenic or antigenic activity of the peptide;
n=1–5;
o=1–5 if c is present, otherwise o=1;
p=1–5;
q=1–5;
r=1–5 if d is present, otherwise r=1; and
s=1–5.

As used herein "analogues" denote amino acid insertions, deletions, substitutions and modifications at one or more sites in the peptide chain in that portion of it that consists of the block of the naturally occurring HTLV-I or HTLV-II amino acid sequences.

Preferred modifications and substitutions to the native amino acid sequence of the peptides of this invention are conservative ones (i.e., those having minimal influence on the secondary structure and hydropathic nature of the peptide). These include substitutions such as those described by Dayhoff in the Atlas of Protein Sequence and Structure 5, 1978 and by Argos in EMBO J. 8, 779–785, 1989. For example, amino acids belonging to one of the following groups represent conservative changes: ala, pro, gly, glu, asp, gln, asn, ser, thr; cys, ser, tyr, thr; val, ile, leu, met, ala, phe; lys, arg, his; and phe, tyr, trp, his. In like manner, methionine, an amino acid which is prone to oxidation may be replaced by norleucine. The preferred substitutions also include substitutions of D-isomers for the corresponding L-amino acids.

However, as described above, irrespective of such insertions, deletions, substitutions and modifications, the peptides of this invention must contain at least six amino acids taken as a block from one of the following: $AA_{283}$-$AA_{309}$ of the gp46 env protein (HTLV-I); $AA_{273}$–$AA_{305}$ of the gp46 product of the env gene (HTLV-II); $AA_{236}$–$AA_{257}$ of the p24 product of the gag protein (HTLV-I); $AA_{242}$–$AA_{263}$ of the p24 product of the gag protein (HTLV-II); and $AA_{171}$–$AA_{207}$ of the gp46 product of the env protein (HTLV-II). Likewise, the tandem peptides of this invention must contain at least six amino acids taken as a block from J and U as defined above.

Preferably, in the peptide formulas of this invention, block sequences X1, X2, Z1, Z2, B2, J and U are sequences of at least 10 amino acids. More preferably, they are sequences of at least 15 amino acids. Even more preferably, they are sequences of at least 20 amino acids and most preferably, they are sequences of at least 25 amino acids. Preferably, in the tandem peptide formula of this invention, n, o, p, q, r and s=1–3. More preferably, n, o, p, q, r and s=1–2.

The term "amino acid" as employed in this description (e.g., in the definition of a and b) except when referring to the amino acid sequence of the gene products of the HTLV-I or HTLV-II, encompasses all of the natural amino acids, those amino acids in their D-configurations, and the known non-native, synthetic, and modified amino acids, such as homocysteine, ornithine, norleucine and β-valine.

The term "block" as used herein refers to a sequence of amino acids identical to that present in a native polypeptide of HTLV-I or HTLV-II.

As reflected in (vi) above, it is within the scope of this invention to employ tandem peptides. These peptides may be homopolymers, copolymers or multimers. We have unexpectedly found that these tandem peptides show a very high degree of reactivity to HTLV antibodies. Physical mixtures of the peptides and tandem peptides of this invention are also within its scope.

Illustrative of peptides of this invention that are derived from gp46 of the env gene of HTLV-I is:

BCH-416 a-(SEQ ID NO:5)-b env(283–309)

wherein the cysteine residue in position 289 was replaced by a serine and also wherein a and b are as defined above.

Illustrative of peptides of this invention derived from gp46 of the env gene of HTLV-II are:

BCH-219 a-(SEQ ID NO: 6)-b env(186-207)

BCH-404 a-(SEQ ID NO: 7)-b env(281-299)

BCH-407 a-(SEQ ID NO: 8)-b env(273-299)

BCH-418 a-(SEQ ID NO: 9)-b env(281-305)

BCH-447 a-(SEQ ID NO: 10)-b env(171-201)

BCH-486 a-(SEQ ID NO: 11)-b env(173-196)

and

BCH-456 a-(SEQ ID NO: 12)-b env(173-186-L-187-196)

wherein a and b are as defined above.

Illustrative of the peptides of this invention derived from p24 of the gag gene of HTLV-I is:

BCH-411 a-(SEQ ID NO:13)-b gag(236–257)

wherein a and b are as defined above.

Illustrative of the peptides derived from p24 of the gag gene of HTLV-II is:

BCH-412 a-(SEQ ID NO:14)-b gag(242–263)

wherein a and b are as defined above.

The preferred tandem peptides of this invention are defined by the formula:

a—J—c—U—b wherein a, b, c, J and U are as defined above. Most preferably, one of J and U is selected from an HTLV-I peptide and the other is selected from an HTLV-II peptide. Illustrative of these preferred tandem peptides is:

BCH-234 a-(SEQ ID NO:15)-b wherein:

J is BCH-152 (SEQ ID NO:16) (derived from the env gene of HTLV-I: env (193–210)) to which a Pro residue was added at the N-terminus (a) and a Leu residue at the C terminus was removed, c not being present and U being BCH-228 (SEQ ID NO:17) (derived from the gag gene of HTLV-I:, gag (120–130), the last 11 amino acids of p19 (FIG. 2)).

The preferred peptides of this invention are BCH-219, BCH-407, BCH-416, BCH-418, BCH-447, BCH-456, BCH-486 and tandem peptide BCH-234. The most preferred peptides of this invention are BCH-416, BCH-456, BCH-486 and BCH-234. The preferred peptide mixture of this invention contains at least BCH-416. More preferably, it contains at least BCH-416 and BCH-234 and most preferably, it contains at least BCH-416, BCH-234 and BCH-456.

In addition to their use in HTLV-I and II diagnostic means, methods and compositions, the peptides of this invention may also be used to distinguish and HTLV-I infection from an HTLV-II infection. Such diagnostic distinction is done, for example, by testing the sample separately with an HTLV-I derived peptide of this invention, or mixture thereof with other HTLV-I peptides and with an HTLV-II derived peptide of this invention or mixture thereof with other HTLV-II peptides and determining which peptide reacts most strongly. The preferred peptides for such methods are BCH-234 for the identification of an HTLV-I infection and BCH-456 and BCH-486 for the identification of an HTLV-II infection.

The peptides of this invention and mixtures thereof are also useful in vaccines against HTLV infections. Antibody titers against HTLV-I and II are notoriously low indicating that these viruses are not very immunogenic or bear immunosuppressive epitopes dampening the normal immune response. Use of synthetic peptides mimicking only those epitopes responsible for the induction of neutralizing antibodies may, thus, be of value in the development of candidate synthetic vaccines. Therefore, it is also within the scope of this invention to use these peptides in vaccines against HTLV-I and HTLV-II infections.

An unexpected advantage of the peptides and mixtures of this invention is their high sensitivity. They are capable of detecting HTLV-I/II-specific antibodies in the majority, and sometimes in all, of confirmed seropositive samples present in a commercial panel sold for the assessment of the performance of anti-HTLV-I/II kits. Another advantage of the peptides and mixtures of this invention is their high level of specificity—a minimal number of false positives. For example, using the above described peptide mixture (BCH-219, BCH-234 and BCH-416) no false-positive was recorded when 150 samples taken from the normal blood donor population were tested. Moreover, average ratio of O.D. recorded upon cut off was equal to 0.25 for these negative samples.

As set forth briefly above, it is often useful and certainly within the scope of this invention to modify the peptides of this invention in order to make the chosen peptide more useful as an immunodiagnostic reagent or as an active ingredient of a vaccine. Such changes, for example, include:

addition of a cysteine residue to one or both terminals in order to facilitate coupling of the peptide to a suitable carrier with heterobifunctional cross-linking reagents such as sulfosuccinimidyl-4-(p-maleimidophenyl) butyrate, preferred reagents for effecting such linkages are sulfosuccinimidyl- sulfosuccinimidyl-4-(N-maleimidomethyl)cyclohexane-1-carboxylate and N-succinimidyl-3-(2-pyridyldithio) propionate;

addition of 1 to 8 additional amino acids at one or both terminals of the peptide to facilitate linking of the peptides to each other, for coupling to a support or larger peptide or protein or for modifying the physical or chemical properties of the peptide. Examples of such changes are the addition of N- or C-terminal tyrosine, glutamic acid or aspartic acid as linkers via an esterification reaction and lysine which can be linked via Schiff base or amide formation. As described above such additional amino acids may include any of the natural amino acids, those amino acids in their D-configurations, and the known non-native, synthetic and modified amino acids; and derivatization of one or both terminals of the peptide by, for example, acylation or amidation. These modifications result in changes in the net charge on the peptide and can also facilitate covalent linking of the peptide to a solid support, a carrier or another peptide. Examples of the substituents effective to facilitate coupling or to improve the immunogenicity or antigenic activity of the peptide are $C_2$–$C_{16}$ acyl groups, polyethylene glycol and phospholipids.

To prepare the novel peptides of this invention any of the conventional peptide production methodologies may be used. These include synthesis, recombinant DNA technology and combinations thereof. We prefer solid phase synthesis. In that synthetic approach, the resin support may be any suitable resin conventionally employed in the art for the solid phase preparation of peptides. Preferably, it is a p-benzyloxyalcohol polystyrene or p-methylbenzydrylamine resin. Following the coupling of the first protected amino acid to the resin support, the amino protecting group is removed by standard methods conventionally employed in the art. After removal of the amino protecting group, the remaining protected amino acids and, if necessary, side chain protected amino acids are coupled, sequentially, in the desired order to obtain the chosen peptide. Alternatively, multiple amino acid groups may be coupled using solution methodology prior to coupling with the resin-supported amino acid sequence.

The selection of an appropriate coupling reagent follows established art. For instance, suitable coupling reagents are N,N'-diisopropylcarbodiimide or N,N'-dicyclohexylcarbodiimide (DCC) or benzotriazol-1-yloxy-tris(dimethylamino)phosphonium hexafluorophosphate either alone or preferably in the presence of 1-hydroxybenzotriazole. Another useful coupling procedure employs preformed symmetrical anhydrides of protected amino acids.

The necessary α-amino protecting group employed for each amino acid introduced onto the growing polypeptide chain is preferably 9-fluorenylmethyloxycarbonyl (FMOC), although any other suitable protecting group may be employed as long as it does not degrade under the coupling conditions and is readily removable selectively in the presence of any other protecting group already present in the growing peptide chain.

The criteria for selecting protecting groups for the side chain amino acids are: (a) stability of the protecting group to the various reagents under reaction conditions selective for the removal of the α-amino protecting group at each step of the synthesis; (b) retention of the protecting group's strategic properties (i.e., not be split off under coupling conditions) and (c) removability of protecting group easily upon conclusion of the peptide synthesis and under conditions that do not otherwise affect the peptide structure.

The fully protected resin-supported peptides are preferably cleaved from the p-benzyloxy alcohol resin with 50% to 60% solution of trifluoroacetic acid in methylene chloride for 1 to 6 hours at room temperature in the presence of appropriate scavengers such as anisole, thioanisole, ethyl methyl sulfide, 1,2-ethanedithiol and related reagents. Simultaneously, most acid labile side-chain protecting groups are removed. More acid resistant protecting groups are typically removed by HF treatment.

The peptides of the present invention are useful as diagnostic reagents for the detection and quantification of HTLV-I and HTLV-II-associated antibodies in accordance with methods well-known in the art. These include ELISA, hemagglutination, single-dot and multi-dot methods and assays.

A preferred convenient and classical technique for the determination of antibodies against the HTLV-I and HTLV-II using a peptide or a peptide mixture of this invention is an enzyme-linked immunosorbent assay (ELISA). In this assay, for example, a peptide or mixture of this invention is adsorbed onto, or covalently coupled to, the wells of a microtiter plate. The wells are then treated with the sera or analyte to be tested. After washing, anti-human IgG or anti-human IgM labeled with peroxidase is added to the wells. The determination of the peroxidase is performed with a corresponding substrate, e.g., 3,3',5,5'-tetra-methylbenzidine. Without departing from the usefulness of this illustrative assay, the peroxidase can be exchanged by another label, e.g., by a radioactive, fluorescence, chemiluminescence or infra-red emitting label.

Another method for the determination of antibodies against the HTLV-I and HTLV-II with the peptides and mixtures of this invention is an enzyme immunological test according to the so-called "Double-Antigen-Sandwich-Assay". This method is based on the work of Maiolini, as described in Immunological Methods, 20, 25–34, 1978. According to this method, the serum or other analyte to be tested is contacted with a solid phase on which a peptide of this invention has been coated (capture layer) and with a peptide of this invention which has been labeled with peroxidase or other label (probe layer).

The immunological reaction can be performed in one or two steps. If the immunological reaction is performed in two steps, then a washing step is typically carried out between the two incubations. After the immunological reaction or reactions, a washing step is also usually performed. Thereafter, the peroxidase or other signal is determined, e.g., using o-phenylene diamine for peroxidase. Other enzymes and chromogens, including those already described, can also be employed in this assay.

Suitable solid phases for use in the above-described assays and assay methods include organic and inorganic polymers, e.g., amylases, dextrans, natural or modified celluloses, polyethylene, polystyrene, polyacrylamides, agaroses, magnetite, porous glass powder, polyvinylidene fluoride (kynar) and latex, the inner wall of test vessels (i.e., test tubes, titer plates or cuvettes of glass or artificial material) as well as the surface of solid bodies (i.e., rods of glass and artificial material, rods with terminal thickening, rods with terminal lobes or lamellae). Spheres of glass and artificial material are especially suitable as solid phase carriers.

The peptides and mixtures of this invention are not only useful in the determination and quantification of antibodies against the HTLV-I and HTLV-II. They are also useful for the determination and quantification of HTLV-I and HTLV-II antigens themselves because the peptides of this invention, either free, polymerized or conjugated to an appropriate carrier, are useful in eliciting antibodies, in particular and preferably, monoclonal antibodies, immunologically cross reactive to the antigens of the HTLV-I and HTLV-II. Such antibodies, for example, can be produced by injecting a mammalian or avian animal with a sufficient amount of the peptide to elicit the desired immune response and recovering said antibodies from the serum of said animals. Suitable host animals for eliciting antibodies include, for example, rabbits, horses, goats, guinea pigs, rats, mice, cows, sheep and hens. Preferably, hybridomas producing the desired monoclonal antibodies are prepared using the peptides of this invention and conventional techniques.

For example, the well-known Kohler and Milstein technique for producing monoclonal antibodies may be used. In order to distinguish monoclonal antibodies which are directed against the same antigen, but against different epitopes, the method of Stähli et al. (J. of Immunological Methods, 32, 297–304, 1980) can be used.

Various methods which are generally known can be employed in the determination or quantification of the HTLV-I and HTLV-II or a portion thereof using the above antibodies. In one such procedure, known amounts of a serum sample or other analyte to be assayed, a radiolabeled peptide or mixture of this invention and an unlabeled peptide or mixture of this invention are mixed together, a given amount of an antipeptide antibody, preferably a monoclonal antibody, is added and the mixture allowed to stand. The resulting antibody/antigen complex is then separated from the unbound reagents by procedures known in the art, i.e., by treatment with ammonium sulphate, polyethylene glycol, a second antibody either in excess or bound to an insoluble support, or dextran-coated charcoal. The concentration of the labeled peptide is then determined in either the bound or unbound phase and the HTLV-I or HTLV-II antigen content of the sample determined by comparing the level of labeled component to a standard curve in a manner known per se.

Another suitable method for using these antibodies in assays is the "Double-Antibody-Sandwich-Assay". According to this assay, the sample to be tested is treated with two different antibodies, e.g., raised by immunizing different animals, e.g., sheep and rabbits, with a peptide or mixture of this invention. One of the antibodies is labeled and the other is coated on a solid phase. The preferred solid phase is a plastic bead and the preferred label is horse-radish peroxidase.

Typically in the "Double-Antibody-Sandwich-Assay", the sample is incubated with the solid phase antibody and the labeled antibody. However, it is also possible to contact the sample first with the solid phase antibody and then, after an optional washing, to contact the sample with the labeled antibody. Preferably, however, the sample is treated together with the solid phase and the labeled antibody. After the immunological reaction(s), the mixture is washed and the label is determined according to procedures known in the art. In the case where peroxidase is used as the label, the determination may be performed using a substrate, e.g., with o-phenylene diamine or with tetramethylbenzidine. The amount of the labeled component is proportional to the amount of the antigen(s) present in the analyte or serum sample.

The methods and assays for the determination and quantification of HTLV-I and HTLV-II antigens or antibodies against those viruses, as described above, can also be conducted in suitable test kits characterized by a peptide or mixture of this invention, or antibodies against HTLV-I or HTLV-II elicited by those peptides and mixtures.

As described above, the peptides and mixtures of this invention are also useful as the active component of vaccines capable of inducing protective immunity against the HTLV-I and HTLV-II in hosts susceptible to infection with those viruses. Routes of administration, antigen doses, number and frequency of injections will vary from individual to individual and parallel those currently being used in providing immunity to other viral infections. For example, the vaccines of this invention are pharmaceutically acceptable compositions containing at least one peptide or mixture of this invention in an amount effective in the mammal, including a human, treated with that composition to raise antibodies sufficient to protect the treated mammal from a HTLV-I or HTLV-II infection for a period of time.

The vaccines are prepared in accordance with known methods. The vaccine compositions of this invention may be conveniently and conventionally combined with physiologically acceptable carrier materials, such as pharmaceutical grade saline, tetanus toxoid, and keyhole limpet hemocyanin. The vaccine compositions of this invention may also contain adjuvants or other enhancers of immune response, such as alum preparations, liposomes or immunomodulators. Furthermore, these vaccine compositions may comprise other antigens to provide immunity against other viruses (e.g., HIV-1 and HIV-2, cytomegalovirus) or pathogens in addition to HTLV-I or HTLV-II. The amount of these other antigens is again dependent on the mammal to be treated and the course of the disease. However, the antigen should be present in an amount effective to raise antibodies sufficient to protect the treated mammal from that pathogen or virus for a period of time.

General procedures for the synthesis and utilization of the peptides of this invention are provided below.

PROCEDURE 1

Preparation of Resins Carrying the N-FMOC Protected Amino Acid Residue

The desired N-FMOC protected amino acid residue in a mixture of methylene chloride ($CH_2Cl_2$) and dimethylformamide (DMF) (4:1) was added to a suspension of p-benzyloxy alcohol resin in $CH_2Cl_2$:DMF (4:1) at 0° C. The mixture was stirred manually for a few seconds and then treated with N,N'-dicyclohexyl-carbodiimide (DCC) followed by a catalytic amount of 4-(dimethylamino) pyridine. The mixture was stirred at 0° C. for an additional 30 minutes and then at room temperature overnight. The filtered resin was washed successively with $CH_2Cl_2$, DMF and isopropanol (3 washes each) and finally, with $CH_2Cl_2$. The resin was suspended in $CH_2Cl_2$, chilled in an ice bath and redistilled pyridine was added to the stirred suspension followed by benzoyl chloride. Stirring was continued at 0° C. for 30 minutes and then at room temperature for 60 minutes. After filtration, the resin was washed successively with $CH_2Cl_2$, DMF and isopropanol (3 washes each) and finally with petroleum ether (twice) before being dried under high vacuum to a constant weight.

Spectrophotometric determination of substitution according to Meienhofer et al. (Int. J. Peptide Protein Res., 13, 35, 1979) indicates the degree of substitution on the resin.

PROCEDURE 2

Coupling of Subsequent Amino Acids

The resin carrying the N-FMOC protected first amino acid residue was placed in a reaction vessel of a Biosearch 9600 Peptide Synthesizer and treated as follows:

1) Washed with DMF (4 times for 20 sec. each)
2) Prewashed with a 30% solution of piperidine in DMF (3 min.)
3) Deprotected with a 30% solution of piperidine in DMF (7 min.)
4) Washed with DMF (8 times for 20 sec. each)
5) Checked for free amino groups—Kaiser Test (must be positive)
6) The peptide resin was then gently shaken for 1 or 2 hrs with 8 equivalents of the desired FMOC-protected amino acid and 1-hydroxybenzotriazole and benzotriazol-1-yloxy-tris(dimethyl-amino)phosphonium hexafluorophosphate all dissolved in dry redistilled DMF containing 16 equivalents of 4-methylmorpholine.
7) Washed with DMF (6 times for 20 sec. each)

After step 7, an aliquot was taken for a ninhydrin test. If the test was negative, one goes back to step 1 for coupling of the next amino acid. If the test was positive or slightly positive, steps 6 and 7 should be repeated.

The above scheme may be used for coupling each of the amino acids of the peptides described in this invention. N-protection with FMOC may also be used with each of the remaining amino acids throughout the synthesis.

Radiolabeled peptides may be prepared by incorporation of a tritiated amino acid using the above coupling protocol.

After the addition of the last amino acid, the N-FMOC of the N-terminal residue is removed by going back to steps 1-7 of the above scheme. The peptide resin is washed with $CH_2Cl_2$ and dried in vacuo to give the crude protected peptide.

PROCEDURE 3

Deprotection and Cleavage of the Peptides from the Resin

The protected peptide-resin was suspended in a 55% solution of trifluoroacetic acid (TFA) in $CH_2Cl_2$, containing 2.5% ethanedithiol and 2.5% anisole. The mixture was flushed with $N_2$ and stirred for 1.5 hours at room temperature. The mixture was filtered and the resin washed with $CH_2Cl_2$. The resin was treated again with 20% TFA in $CH_2Cl_2$ for 5 minutes at room temperature. The mixture was filtered and the resin washed with 20% TFA in $CH_2Cl_2$ and then washed with $CH_2Cl_2$. The combined filtrates were evaporated in vacuo below 35° C. and the residue triturated several times with dry dimethyl ether. The solid was dissolved in 10% aqueous acetic acid and lyophilized to afford the crude product.

The peptides containing arg and cys residues are further deprotected by HF treatment at 0° C. for 1 hour in the presence of anisole and dimethylsulfide. The peptides were extracted with 10% aqueous acetic acid, washed with dimethyl ether and lyophilized to afford the crude peptides.

PROCEDURE 4

Purification of Peptides

The crude peptides were purified by preparative HPLC on a Vydac column (2.5×25 mm) of $C_{18}$ or $C_4$ reverse phase with a gradient of the mobile phase. The effluent was monitored at 220 nm and subsequently by analytical HPLC. Relevant fractions were pooled, evaporated and lyophilized. The identity of the synthetic peptides was verified by analytical reverse phase chromatography and by amino acid analysis.

PROCEDURE 5

Conjugation of Peptides to Bovine Serum Albumin or Keyhole Limpet Hemocyanin Peptides were conjugated to BSA or KLH previously derivatized with either sulfosuccinimidyl 4-(p-maleimidophenyl) butyrate (Sulfo-SMPB) or sulfosuccinimidyl 4-(N-maleimidomethyl) cyclohexane-1-carboxylate (Sulfo-SMCC).

An aqueous solution of sulfo-SMPB or sulfo-SMCC (Pierce Chemicals) was added to a solution of BSA or KLH in 0.02M sodium phosphate buffer (pH 7.0). The mixture was shaken at room temperature for 45 minutes and the activated carrier immediately applied to a Sephadex G-25 column equilibrated with 0.1M sodium phosphate buffer (pH 6.0) at 4° C.

The fractions of the first peak absorbance (280 nm) corresponding to activated carrier were combined in a round bottom flask to which was added a solution of peptide in 0.05M sodium phosphate buffer (pH 6.2). The mixture was thoroughly flushed with $N_2$ and incubated overnight at room temperature. The coupling efficiency was monitored using 3H-labeled peptide and by amino acid analysis of the conjugate.

PROCEDURE 6

Detection of Antibodies to HTLV-I or HTLV-II by an Enzyme Linked Immunosorbent Assay (ELISA)

Each well of the microtiter plate was saturated with 100 1 of a solution containing a peptide or mixture of peptides (10 µg/ml) and left overnight. The wells were emptied and washed twice with a washing buffer (Tris, 0.043M; NaCl, 0.5M; thimerosal, 0.01% w/v; Tween 20, 0.05% v/v; pH 7.4). The wells were then saturated with 0.35 ml of washing buffer for 1 hour at 37° C. and washed once with the same buffer. Serum samples to be analyzed were diluted with specimen buffer (washing buffer plus casein, 0.05% w/v). The wells were rinsed with washing buffer prior to the addition of the diluted serum sample (0.1 ml). These were left to incubate for 1 hour at room temperature. The wells were then emptied, washed twice rapidly and then once for two minutes with washing buffer. The conjugate solution (peroxidase labeled affinity purified goat antibody to human IgG or to human IgM, 0.5 mg in 5 ml 50% glycerol) diluted with 1% w/v bovine serum albumin in washing buffer was added to each well (0.1 ml) and incubated for 1 hour at room temperature. The wells were then emptied and washed five times with the washing buffer. The substrate solution (3,3′,5,5′-tetramethylbenzidine, 8 mg per ml of DMSO) was diluted with 100 volumes 0.1M citrate-acetate buffer (pH 5.6) containing 0.1% v/v of 30% $H_2O_2$ and added to each well (0.1 ml per well). After 30 minutes, the contents of each well were treated with 0.1 ml 2N $H_2SO_4$ and the optical density read at 450 nm. All determinations were done in duplicate.

Using general procedures substantially as described above, the following specific peptides were prepared: BCH-152, BCH-219, BCH-221, BCH-228, BCH-234, BCH-296, BCH-298, BCH-404, BCH-407, BCH-411, BCH-412, BCH-416, BCH-418, BCH-447, BCH-456 and BCH-486. These peptides were then evaluated for their ability to detect HTLV-I and HTLV-II-specific antibodies.

EXPERIMENT 1

In Experiment 1 individual peptides BCH-152, BCH-228, a cocktail formed by the mixture of equal amounts of BCH-152 and BCH-228, and individual peptide BCH-234 were compared in ELISA assays using a panel of seropositive and seronegative serum and plasma samples. BCH-234 is a tandem peptide wherein BCH-152 (with a Pro residue at the N-terminus) is attached to BCH-228. The results represent signal to cut off ratios and are displayed in Table 1.

TABLE 1

| SERUM NO. | W.B. | EIA WITH SYNTHETIC PEPTIDE | | | |
|---|---|---|---|---|---|
| | | 152 | 228 | 152 + 228 | 234 |
| BBI-168 | NEG | 0.50 | 0.58 | 0.50 | 0.44 |
| SC1*1/250 | POS | 8.71 | 5.94 | — | 13.5 |
| B-12 | POS | 1.60 | 2.12 | 1.80 | 3.78 |
| B-14 | POS | 0.85 | 6.37 | 2.10 | 11.5 |
| B-18 | POS | 0.50 | 1.75 | 0.95 | 3.72 |
| B-20 | POS | 0.45 | 6.33 | 1.55 | 11.7 |
| B-21 | POS | 0.40 | 2.58 | 1.00 | 9.67 |
| B-22 | POS | 0.50 | 1.58 | 0.55 | 9.89 |
| B-23 | POS | 2.75 | 3.42 | 2.70 | 9.67 |
| B-27 | POS | 2.11 | 2.79 | 2.45 | 7.17 |
| B-30 | POS | 10.4 | 2.04 | 9.85 | 10.7 |
| B-31 | POS | 1.55 | 5.08 | 2.10 | 12.8 |
| A02-1 | POS | | 0.39 | 0.45 | 0.30 |
| A02-2 | POS | >14 | 13.7 | | >14 |
| A02-3 | POS | | 0.34 | 0.34 | 0.21 |
| A02-4 | POS | | 0.75 | 0.76 | 0.40 |
| A02-5 | POS | | 0.32 | 0.39 | 0.28 |
| A02-6 | IND** | | 0.38 | 0.36 | 0.23 |
| A02-7 | POS | | 0.89 | 0.79 | 2.72 |
| A02-8 | POS | | 0.52 | 0.63 | 0.43 |
| A02-9 | POS | | 0.78 | 0.66 | 0.47 |
| A02-10 | POS | 8.71 | 4.73 | | 10.5 |

**Indeterminable

In Table 1, the samples labeled B- were obtained from Japan and those labeled BBI-168, SC1* 1/250 and A02- are from the U.S. As mentioned above, infected American samples have antibody titers that are lower than those measured in blood samples from Japan.

In this experiment, the cut off above which a sample was considered positive for the presence of antibodies to HTLV-I and HTLV-II was defined as being equal to the O.D. value obtained with the negative control sample (BBI-168) plus 0.10. Results shown are signal to cut off ratios. Serum samples giving a ratio equal or above 1.0 are considered as positive.

Peptide BCH-152 recognized 8 of these 21 HTLV-I/HTLV-II seropositive samples. Peptide BCH-228 detected 14 out of 21 samples. Although peptide BCH-228 could detect all samples obtained from Japan (albeit with relatively low titers), it detected only two of the ten American samples. The origin of the sera thus lead to a net difference in sensitivity using these individual peptides.

Because peptides BCH-152 and BCH-228 represent distinct epitopes of the HTLV-I virus, we mixed them in an attempt to augment the sensitivity of detection. As indicated in Table 1, the signal measured with the mixture was, in all cases, lower than the signal measured with the best of the two peptides taken singly. There is, thus, no observed additive effect when these two peptides were mixed together.

Surprisingly, a tandem of these two peptides, e.g., peptide BCH-234, dramatically augmented the sensitivity of detection of antibodies to HTLV-I/II. In all cases, the signal/cut off ratio recorded was higher with tandem peptide BCH-234 than with the individual peptides or cocktail. BCH-234 detected 15 of the 21 samples tested. Furthermore, in addition to being able to detect an extra sample on the American panel (A02-7), the signal/cutoff ratios measured on the Japanese panel (B-series) with BCH-234 were, in all cases, higher than those obtained with the individual peptides.

EXPERIMENT 2

In Experiment 2, peptides BCH-219, BCH-221, BCH-296 and BCH-298 were tested in an ELISA using a panel of seropositive and seronegative serum and plasma samples obtained from Boston Biomedica Inc. (all U.S. strains).

The results represent signal to cut off ratios and are displayed in Table 2.

TABLE 2

| SERUM NO. | W.B. | EIA WITH SYNTHETIC PEPTIDE | | | |
|---|---|---|---|---|---|
| | | 219 | 221 | 298 | 296 |
| BBI-163 | NEG | 0.20 | 0.33 | 0.50 | 0.21 |
| SC1*1/250 | POS | 0.30 | 0.39 | 12.74 | 9.50 |
| A02-1 | POS | 11.8 | 0.41 | 4.50 | 3.71 |
| A02-2 | POS | 0.55 | 0.71 | >14 | >14 |
| A02-3 | POS | 1.20 | 0.38 | 0.85 | 0.38 |
| A02-4 | POS | 0.55 | 0.61 | 2.30 | 0.62 |
| A02-5 | POS | 1.15 | 0.53 | 2.85 | 1.67 |
| A02-6 | IND | 0.40 | 0.35 | 0.60 | 0.42 |
| A02-7 | POS | 0.35 | 0.48 | 9.45 | 7.71 |
| A02-8 | POS | 4.15 | 0.52 | 1.65 | 1.00 |

TABLE 2-continued

| SERUM NO. | W.B. | EIA WITH SYNTHETIC PEPTIDE | | | |
|---|---|---|---|---|---|
| | | 219 | 221 | 298 | 296 |
| A02-9 | POS | 11.5 | 0.51 | 1.25 | 0.75 |
| A02-10 | POS | 0.55 | 0.55 | 12.6 | 8.92 |
| A02-11 | IND | 4.40 | 0.57 | 4.35 | 2.75 |
| A02-12 | POS | 1.15 | 0.44 | 2.85 | 1.83 |
| A02-13 | IND | 0.80 | 0.43 | 1.45 | 1.04 |
| A02-14 | POS | 9.75 | 0.44 | 12.1 | 8.71 |
| A02-15 | POS | 3.30 | 0.37 | 6.00 | 2.71 |
| A02-16 | POS | 1.60 | 0.41 | 3.00 | 2.04 |
| A02-17 | IND | 0.80 | 0.39 | 1.20 | 2.75 |
| A02-18 | POS | 3.20 | 3.68 | 11.1 | 1.46 |
| A02-19 | POS | 10.0 | 0.41 | 0.85 | 2.21 |
| A02-20 | POS | 0.45 | 0.34 | >14 | >14 |
| A02-21 | POS | 4.85 | 0.38 | 3.05 | 2.71 |
| A02-22 | POS | 4.60 | 0.36 | 4.00 | 2.25 |
| A02-23 | IND | 5.15 | 0.54 | 3.95 | 2.33 |
| A02-24 | POS | >14 | 0.35 | 13.6 | 3.12 |
| A02-25 | POS | 2.55 | 0.49 | 1.75 | 1.21 |

Peptide BCH-219 detected 17 out of the 26 seropositive samples tested. More importantly, peptide BCH-219 could detect the presence of HTLV antibodies in samples that were not detectable with BCH-234 (see Table 1). Peptide BCH-298 (a-TTDNSNNSIILPPFSLAPVPPP ATRRRR-b; HTLV-II env 281–308), which is a longer version of peptide BCH-221 and which has a serine residue at position 285 instead of the natural cysteine residue (this was done to avoid dimerization of the peptide, to increase its stability and to increase the specificity of the test), detected 23 out of 26 samples. This latter result illustrates the importance of residues env(281–292) which are absent on the poorly performing peptide BCH-221 (a-PFSLAPVPPPATRRRR-b HTLV-II env(293–308)) and which contribute largely to the increased antigenicity of peptide BCH-298. Peptide BCH-296 (a-AIVSSPSHNSLILPPFSLSPVPTLGSRSRR-b HTLV-I env (283–312)) detected 22 out of 26 samples but the signals were in general lower than those obtained when using BCH-298. It was later found, however, that when peptides BCH-298 or BCH-296 were used in a cocktail, they were responsible for the detection of a large number of false positives. For example, the screening of 500 samples obtained from normal blood donors lead to 38 putative seropositives when BCH-298 was part of a three-peptide cocktail. Different peptide analogs were synthesized in order to identify and eliminate the regions on BCH-298 and on BCH-296 which were responsible for these non-specific responses. Peptides BCH-404, BCH-407, BCH-416 and BCH-418 were particularly useful to achieving this goal (see Table 3).

EXPERIMENT 3

In Experiment 3, solutions prepared with each of the following peptides: BCH-404, BCH-407, BCH-416 and BCH-418, at 10 μg/ml, were used to coat EIA plates as described above. A cocktail of peptides was also prepared by the mixing of equal volumes of three of the peptide solutions described above (BCH-219, BCH-234 and BCH-416) and used to coat another series of plates. All seropositive samples tested were obtained from Boston Biomedica Inc.

The results represent signal to cut off ratios and are displayed in Table 3. In this experiment the cut off (0.20) is the average O.D. measured on 50 samples taken from the normal blood donor population to which were added 4 standard deviations. (Cut off=$X_{NEG}$+4 S.D.)

TABLE 3

| SERUM No. | EIA WITH SYNTHETIC PEPTIDE | | | | |
|---|---|---|---|---|---|
| | 404 | 407 | 416 | 418 | 219 + 234 + 416 |
| A02-01 | 0.74 | 0.81 | 7.17 | 9.21 | >23.33 |
| A02-02 | >10.37 | >23.33 | >23.33 | >23.33 | >23.33 |
| A02-03 | 0.63 | 0.31 | 0.38 | 0.38 | 1.20 |
| A02-04 | 0.87 | 1.13 | 6.25 | 0.99 | 6.31 |
| A02-05 | 0.81 | 1.34 | 2.42 | 5.26 | 7.46 |
| A02-06 | 0.66 | 0.23 | 0.24 | 0.16 | 0.66 |
| A02-07 | 7.20 | 18.78 | 18.33 | 22.92 | >23.33 |
| A02-08 | 0.67 | 0.63 | 2.53 | 2.45 | 7.42 |
| A02-09 | 0.96 | 1.58 | 7.93 | 1.72 | >23.33 |
| A02-10 | 1.15 | 7.17 | 22.33 | >23.33 | >23.33 |
| A02-11 | 0.68 | 1.39 | 7.80 | 7.78 | 16.77 |
| A02-12 | 0.77 | 1.53 | 2.74 | 6.00 | 7.87 |
| A02-13 | 0.63 | 0.49 | 2.02 | 2.37 | 5.77 |
| A02-14 | 5.78 | 15.67 | 22.28 | >23.33 | >23.33 |
| A02-15 | 2.33 | 11.32 | 4.76 | 9.52 | 16.43 |
| A02-16 | 0.71 | 0.43 | 5.38 | 6.17 | 13.39 |
| A02-17 | 0.67 | 0.46 | 1.51 | 1.79 | 2.17 |
| A02-18 | 0.69 | 0.52 | 2.95 | >23.33 | 8.06 |
| A02-19 | 0.65 | 0.37 | 0.80 | 0.66 | 7.17 |
| A02-20 | 1.10 | 10.03 | >23.33 | >23.33 | >23.33 |
| A02-21 | 0.90 | 1.59 | 3.73 | 4.95 | 9.14 |
| A02-22 | 0.91 | 1.48 | 5.86 | 7.13 | 22.23 |
| A02-23 | 1.10 | 1.98 | 5.93 | 6.97 | 18.39 |
| A02-24 | 4.13 | 22.01 | 13.82 | >23.33 | >23.33 |
| A02-25 | 0.83 | 0.98 | 2.17 | 2.56 | 5.87 |

Peptides BCH-404, BCH-407 and BCH-418 were synthesized in order to find one that would keep the same levels of sensitivity as BCH-298 (a-TTDNSNNSIILPPFSLAPVPPPATRRRR-b HTLV-II env (281–308)) but would not lead to false-positive signals. Peptide BCH-418 is as useful as BCH-298 in detecting the seropositive samples and did not give false-positive signals when tested on 500 serum samples taken from normal blood donors. Thus BCH-418 (which is identical to BCH-298 with the exception that the last three arginine residues were absent) is as sensitive as BCH- 298 in detecting HTLV-I and HTLV-II antibodies and also much more specific. A similar observation was made with synthetic peptide BCH-416, which is a shorter version of HTLV-I peptide BCH-296. As a result, we have concluded that these three amino acid residues located near the C-terminal end of the gp46 protein of both HTLV-I and HTLV-II contribute to the binding of antibody molecules not related to HTLV-I and HTLV-II infection.

We also tested a peptide cocktail including a preferred HTLV-I tandem peptide BCH-234 and peptides derived from the sequence of HTLV-II (BCH-219 and BCH-416). The results presented in Table 3 show that this cocktail can surprisingly detect all confirmed HTLV-I and HTLV-II seropositive samples tested. Specimen A02-6, which was found indeterminate by Western Blot and by immunofluorescence (IFA) was found negative in this test. That sample was found weakly positive in one test out of two.

EXPERIMENT 4

In Experiment 4, solutions prepared with synthetic peptides BCH-411 and BCH-412 at 10 μg/ml, were used to coat EIA plates as described above. Samples tested were obtained from Japan.

The results represent signal to cut off ratios and are displayed in Table 4. The cut off in this experiment is the average of O.D. values obtained with three negative samples to which 4 S.D. were added.

TABLE 4

| SERUM No. | EIA WITH SYNTHETIC PEPTIDE | |
|---|---|---|
| | 411 | 412 |
| B-12 | 1.74 | 1.34 |
| B-13 | 3.55 | 1.21 |
| B-14 | 9.84 | 2.42 |
| B-15 | 6.50 | 1.97 |
| B-16 | 2.64 | 2.24 |
| B-17 | 14.43 | 2.26 |
| B-18 | 1.81 | 1.39 |
| B-19 | 2.01 | 1.95 |
| B-20 | 7.17 | 1.47 |
| B-21 | 2.70 | 1.87 |
| B-22 | 1.78 | 1.89 |
| B-23 | 3.51 | 1.05 |
| B-24 | 4.61 | 1.55 |
| B-25 | 2.74 | 2.16 |
| B-26 | 12.09 | 2.24 |
| B-27 | 2.38 | 2.32 |
| B-28 | 10.56 | 1.92 |
| B-29 | 1.90 | 2.26 |
| B-30 | 5.39 | 2.16 |
| B-31 | 34.54 | 3.55 |

EXPERIMENT 5

In Experiment 5, peptides BCH-219, BCH-447, BCH-456 and BCH-486 were tested in ELISA using a panel of seropositive and seronegative serum and plasma samples obtained from Boston Biomedica Inc.

The results (Table 5) represent the signal to cut off ratios. The cut off is the average of the absorbancy values measured with three negative serum samples to which was added 0.100.

Peptide BCH-219 detected 18 out of the 25 seropositive samples tested (Table 5). Two of the samples (No. A02-6 and A02-17) missed by BCH-219 are WB indeterminate. In this experiment, sample A02-2, which was taken from an HTLV-I infected patient was found positive. This was not always the case. In some other experiments, this sample was not detected as positive with BCH-219. Similarly, sample A02-16, which is not detected positive in this experiment, could in other tests be detected by BCH-219.

Peptide BCH-447 detected all HTLV-I and HTLV-II samples tested. Peptide BCH-456 did not detect any of the four HTLV-I samples and was also negative with one WB-indeterminate sample (A02-6). The profile or reactivity of BCH-486 is similar to BCH-456. Although the signals measured with BCH-486 are generally higher than those obtained with BCH-456, the latter is preferred because BCH-486 gave a borderline negative signal (0.94) with one HTLV-II sample (A02-4).

TABLE 5

| SERUM NO. | W.B. | EIA WITH SYNTHETIC PEPTIDE | | | |
|---|---|---|---|---|---|
| | | 219 | 447 | 456 | 486 |
| A02-1 | HTLV-II | 14.99 | 18.75 | 9.09 | 16.67 |
| A02-2 | HTLV-I | 1.91 | 1.81 | 0.60 | 0.50 |
| A02-3 | HTLV-II | 1.62 | 4.38 | 1.91 | 3.50 |
| A02-4 | HTLV-II | 0.73 | 1.50 | 1.30 | 0.94 |
| A02-5 | HTLV-II | 1.19 | 8.25 | 8.45 | 5.00 |
| A02-6 | Ind. | 0.51 | 1.19 | 0.15 | 0.33 |
| A02-7 | HTLV-I | 0.57 | 1.31 | 0.30 | 0.50 |
| A02-8 | HTLV-II | 3.91 | 10.75 | 5.09 | 11.17 |
| A02-9 | HTLV-II | 17.65 | 16.75 | 8.12 | 15.39 |
| A02-10 | HTLV-I | 0.52 | 1.44 | 0.39 | 0.56 |
| A02-11 | HTLV-II | 4.42 | 9.63 | 4.91 | 9.28 |
| A02-12 | HTLV-II | 1.72 | 9.06 | 7.88 | 4.72 |
| A02-13 | Ind. | 1.11 | 2.56 | 5.55 | 1.72 |
| A02-14 | HTLV-II | 10.74 | 15.25 | 8.30 | 16.67 |
| A02-15 | HTLV-II | 3.65 | 6.50 | 3.52 | 6.61 |
| A02-16 | HTLV-II | 0.58 | 12.50 | 6.12 | 12.17 |
| A02-17 | Ind. | 0.86 | 2.06 | 1.36 | 1.50 |
| A02-18 | HTLV-II | 2.95 | 6.81 | 3.15 | 5.61 |
| A02-19 | HTLV-II | 12.83 | 14.38 | 9.09 | 16.67 |
| A02-20 | HTLV-I | 0.64 | 1.25 | 0.12 | 0.22 |
| A02-21 | HTLV-II | 3.68 | 11.31 | 6.18 | 10.50 |
| A02-22 | HTLV-II | 6.45 | 9.69 | 5.33 | 10.78 |
| A02-23 | HTLV-II | 6.20 | 10.44 | 5.48 | 11.33 |
| A02-24 | HTLV-II | 17.65 | 18.75 | 9.09 | 16.67 |
| A02-25 | HTLV-II | 2.62 | 6.31 | 4.94 | 6.39 |

EXPERIMENT 6

In Experiment 6, three cocktails of peptides were prepared (10 μg total peptide/ml of solution) and used to coat EIA plates as described above. The composition of each peptide cocktail and the results obtained are described in Table 6. All samples tested were bought from Boston Biomedica Inc. and the results are expressed as signal to cut off ratios as explained before.

The first cocktail containing BCH-219 did not detect samples A02-4 and A02-6; sample A02-3 was borderline negative. Although sample A02-6 is WB-indeterminate, samples A02-3 and A02-4 are confirmed HTLV-II positive and should not be missed. The third cocktail, containing BCH-447, also missed samples 4 and 6 but could recognize sample A02-3 as positive. The signals recorded with the BCH-447 cocktail were higher than those measured using the BCH-219 cocktail. Finally, the cocktail containing BCH-456 detected all samples confirmed to be HTLV-I or HTLV-II positive and, in most cases, ratios were higher than with the other two cocktails. This experiment showed that a cocktail composed of BCH-234, BCH-456 and BCH-416 gives the best sensitivity in detecting both HTLV-I and HTLV-II seropositive samples.

In this experiment, 36 samples (No. 301 to 336) taken from a normal blood donor population were also tested. All were found negative but sample 310 which gave a strong positive signal when measured on the peptide cocktail containing BCH-219. This sample was later confirmed negative by WB. Finally, another sample, E8-2109-272, was similarly found positive with the BCH-234:BCH-219:BCH-416 cocktail although it was WB negative. This sample did not give a false signal on the other two peptide cocktails thus demonstrating their higher degree of specificity.

Experiment 6 demonstrated the superiority of peptide BCH-447, and more preferably BCH-456, over BCH-219 in increasing both the sensitivity and specificity of a peptide cocktail aimed at detecting HTLV-I and HTLV-II specific antibodies.

TABLE 6

| SERUM NO. | EIA WITH SYNTHETIC PEPTIDE | | |
|---|---|---|---|
| | 234:219:416 | 234:447:416 | 234:456:416 |
| A02-1 | 6.99 | 13.95 | 12.94 |
| A02-2 | 13.95 | 13.95 | 15.00 |
| A02-3 | 0.96 | 1.35 | 1.33 |
| A02-4 | 0.68 | 0.87 | 1.44 |
| A02-5 | 1.40 | 2.24 | 8.45 |
| A02-6 | 0.30 | 0.54 | 0.60 |
| A02-7 | 6.92 | 11.07 | 12.61 |
| A02-8 | 2.75 | 5.71 | 6.06 |
| A02-9 | 13.95 | 13.95 | 12.02 |
| A02-10 | 13.95 | 13.95 | 15.00 |
| A02-11 | 3.73 | 5.51 | 6.65 |

TABLE 6-continued

| SERUM NO. | EIA WITH SYNTHETIC PEPTIDE | | |
|---|---|---|---|
| | 234:219:416 | 234:447:416 | 234:456:416 |
| A02-12 | 1.79 | 2.88 | 9.15 |
| A02-13 | 1.17 | 2.08 | 2.78 |
| A02-14 | 10.71 | 13.95 | 15.00 |
| A02-15 | 3.87 | 5.75 | 7.09 |
| A02-16 | 2.80 | 6.33 | 5.77 |
| A02-17 | 1.13 | 1.69 | 1.54 |
| A02-18 | 2.03 | 2.65 | 3.70 |
| A02-19 | 5.46 | 13.95 | 13.46 |
| A02-20 | 13.95 | 13.95 | 15.00 |
| A02-21 | 2.23 | 3.70 | 5.72 |
| A02-22 | 5.56 | 7.49 | 8.75 |
| A02-23 | 4.61 | 7.90 | 9.20 |
| A02-24 | 13.95 | 13.95 | 15.00 |
| A02-25 | 1.91 | 3.19 | 3.32 |
| 301 | 0.29 | 0.39 | 0.51 |
| 302 | 0.49 | 0.56 | 0.36 |
| 303 | 0.49 | 0.48 | 0.50 |
| 304 | 0.39 | 0.41 | 0.39 |
| 305 | 0.51 | 0.38 | 0.52 |
| 306 | 0.33 | 0.53 | 0.53 |
| 307 | 0.38 | 0.56 | 0.50 |
| 308 | 0.33 | 0.7 | 0.44 |
| 309 | 0.37 | 0.62 | 0.50 |
| 310 | 4.29 | 0.73 | 0.48 |
| 311 | 0.42 | 0.46 | 0.57 |
| 312 | 0.48 | 0.42 | 0.43 |
| 313 | 0.33 | 0.48 | 0.48 |
| 314 | 0.56 | 0.59 | 0.36 |
| 315 | 0.33 | 0.76 | 0.52 |
| 316 | 0.58 | 0.60 | 0.55 |
| 317 | 0.28 | 0.54 | 0.40 |
| 318 | 0.47 | 0.61 | 0.36 |
| 319 | 0.62 | 0.56 | 0.52 |
| 320 | 0.49 | 0.51 | 0.42 |
| 321 | 0.41 | 0.57 | 0.54 |
| 322 | 0.33 | 0.52 | 0.53 |
| 323 | 0.32 | 0.71 | 0.30 |
| 324 | 0.59 | 0.53 | 0.56 |
| 325 | 0.46 | 0.56 | 0.34 |
| 326 | 0.30 | 0.44 | 0.51 |
| 327 | 0.36 | 0.43 | 0.52 |
| 328 | 0.29 | 0.40 | 0.52 |
| 329 | 0.33 | 0.51 | 0.54 |
| 330 | 0.39 | 0.55 | 0.54 |
| 331 | 0.41 | 0.56 | 0.24 |
| 332 | 0.50 | 0.60 | 0.31 |
| 333 | 0.57 | 0.67 | 0.40 |
| 334 | 0.40 | 0.53 | 0.43 |
| 335 | 0.59 | 0.47 | 0.44 |
| 336 | 0.52 | 0.59 | 0.33 |
| E8-2109-272 | 2.68 | 0.77 | 0.51 |

EXPERIMENT 7

In Experiment 7, 25 serum samples obtained from patients identified by polymerase chain reaction (PCR) as being HTLV-I (HT-100 series) or HTLV-II (HT-200 series) carriers were analyzed on plates coated with BCH-234 (HTLV-I specific) or with BCH-219 or BCH-456 (HTLV-II specific). Results displayed in Table 7 are signal to cut off ratios calculated as stated above.

Table 7 illustrates the ease with which peptides BCH-234 and BCH-456 can selectively distinguish samples obtained from a patient infected with HTLV-I from one infected with HTLV-II. Samples from the five HTLV-I infected patients give a strong signal when tested with the HTLV-I specific peptide (BCH-234) and only a low signal on BCH-219. It is noteworthy that these five samples are all negative when tested on the HTLV-II specific peptide BCH-456. Furthermore, the 20 samples taken from HTLV-II infected patients are all easily detected with BCH-456 thus showing its excellent capacity in selectively discriminating samples from HTLV-II infected patients from those taken from an HTLV-I infected one.

TABLE 7

| SERUM NO. | PCR ANALYSIS | EIA WITH SYNTHETIC PEPTIDE | | |
|---|---|---|---|---|
| | | BCH-234 (HTLV-I) | BCH-219 (HTLV-II) | BCH-456 (HTLV-II) |
| HT-101 | HTLV-I | 11.11 | 0.62 | 0.85 |
| HT-102 | HTLV-I | 11.11 | 1.07 | 0.97 |
| HT-103 | HTLV-I | 11.11 | 1.92 | 0.79 |
| HT-104 | HTLV-I | 11.11 | 1.12 | 0.61 |
| HT-105 | HTLV-I | 8.72 | 1.32 | 0.75 |
| HT-201 | HTLV-II | 1.03 | 5.52 | 25.00 |
| HT-202 | HTLV-II | 1.68 | 1.86 | 16.63 |
| HT-203 | HTLV-II | 0.81 | 2.25 | 10.44 |
| HT-204 | HTLV-II | 0.75 | 3.34 | 15.07 |
| HT-205 | HTLV-II | 1.07 | 9.09 | 25.00 |
| HT-206 | HTLV-II | 1.43 | 9.09 | 25.00 |
| HT-207 | HTLV-II | 1.82 | 1.94 | 14.37 |
| HT-208 | HTLV-II | 1.75 | 5.82 | 21.03 |
| HT-209 | HTLV-II | 0.91 | 4.05 | 25.00 |
| HT-210 | HTLV-II | 0.90 | 1.58 | 6.38 |
| HT-211 | HTLV-II | 0.76 | 9.09 | 25.00 |
| HT-212 | HTLV-II | 0.67 | 6.87 | 22.54 |
| HT-213 | HTLV-II | 1.17 | 2.42 | 8.53 |
| HT-214 | HTLV-II | 1.48 | 6.87 | 25.00 |
| HT-215 | HTLV-II | 1.85 | 9.09 | 25.00 |
| HT-216 | HTLV-II | 1.09 | 2.98 | 17.37 |
| HT-217 | HTLV-II | 1.15 | 1.43 | 9.57 |
| HT-218 | HTLV-II | 1.16 | 0.67 | 1.75 |
| HT-219 | HTLV-II | 0.66 | 0.61 | 3.78 |
| HT-220 | HTLV-II | 0.99 | 5.79 | 16.75 |

While we have herein before described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented herein before by way of example.

We claim:

1. A peptide having the formula a-AIVSSPSHNSLILPPFSLSPVPTLGSR-b
    (BCH-416)

wherein:
    a is an amino terminus or a substituent effective to facilitate coupling or to improve the immunogenic or antigenic activity of the peptide; and
    b is a carboxy terminus or a substituent effective to facilitate coupling or to improve the immunogenic or antigenic activity of the peptide; or said peptide which contains deletions or conservative substitutions which do not alter the immunoreactivity of the peptide.

2. A peptide having the formula a-TTDNSNNSIILPPFSLAPVPPPATR-b
    (BCH-418)

wherein:
    a is an amino terminus or a substituent effective to facilitate coupling or to improve the immunogenic or antigenic activity of the peptide; and
    b is a carboxy terminus or a substituent effective to facilitate coupling or to improve the immunogenic or antigenic activity of the peptide; or said peptide which contains deletions or conservative substitutions which do not alter the immunoreactivity of the peptide.

3. A peptide having the formula a—Z1—b wherein:
    Z1 is a sequence of at least six amino acids taken as a block from $AA_{236}$-$AA_{257}$ (SEQ ID NO:13) of the gap p24 protein (HTLV-I);
    a is an amino terminus or a substituent effective to facilitate coupling or to improve the immunogenic or antigenic activity of the peptide; and
    b is a carboxy terminus or a substituent effective to facilitate coupling or to improve the immunogenic or antigenic activity of the peptide; or said peptide which contains deletions or conservative substitutions which do not alter the immunoreactivity of the peptide.

4. A peptide according to claim 3 wherein Z1 is —QQGLRREYQQLWLAAFAALPGS— (BCH-411) (SEQ ID NO:13); or said peptide which contains deletions or conservative substitutions which do not alter the immunoreactivity of the peptide.

5. A peptide of the formula a—Z2—b wherein
    Z2 is a sequence of at least six amino acids taken as a block from $AA_{242}$-$AA_{263}$ (SEQ ID NO:14) of the gag p24 protein (HTLV-II);
    a is an amino terminus or a substituent effective to facilitate coupling or to improve the immunogenic or antigenic activity of the peptide; and
    b is a carboxy terminus or a substituent effective to facilitate coupling or to improve the immunogenic or antigenic activity of the peptide; or said peptide which contains deletions or conservative substitutions which do not alter the immunoreactivity of the peptide.

6. A peptide according to claim 5 wherein Z2 is —QQGLRREYQNLWLAAFSTLPGN— (BCH-412) (SEQ ID NO:14); or said peptide which contains deletions or conservative substitutions which do not alter the immunoreactivity of the peptide.

7. A peptide having the formula a-TSEPTQPPPTSPPLLVHDSDLEHVL-b
    (BCH-456)

wherein:
    a is an amino terminus or a substituent effective to facilitate coupling or to improve the immunogenic or antigenic activity of the peptide; and
    b is a carboxy terminus or a substituent effective to facilitate coupling or to improve the immunogenic or antigenic activity of the peptide; or said peptide which contains deletions or conservative substitutions which do not alter the immunoreactivity of the peptide.

8. A peptide having the formula a-PHSNLDHILEPSIPWKSKPYVEPTAPQVL-b
    (BCH-234)

wherein;
    a is an amino terminus or a substituent effective to facilitate coupling or to improve the immunogenic or antigenic activity of the peptide; and
    b is a carboxy terminus or a substituent effective to facilitate coupling or to improve the immunogenic or antigenic activity of the peptide; or said peptide which contains deletions or conservative substitutions which do not alter the immunoreactivity of the peptide.

9. A peptide having the formula a-TSEPTQPPPTSPPLVHDSDLEHVL-b
    (BCH-456)

wherein:
- a is an amino terminus or a substituent effective to facilitate coupling or to improve the immunogenic or antigenic activity of the peptide; and
- b is a carboxy terminus or a substituent effective to facilitate coupling or to improve the immunogenic or antigenic activity of the peptide; or said peptide which contains deletions or conservative substitutions which do not alter the immunoreactivity of the peptide.

10. A mixture or combination comprising more than one peptide according to any one of claims 1 to 9.

11. The mixture of combination according to claim 10 comprising at least the following peptide:

a-AIVSSPSHNSLILPPFSLSPVPTLGSR-b
    (BCH-416) (SEQ ID NO:5)

wherein
- a is an amino terminus or a substituent effective to facilitate coupling or to improve the immunogenic or antigenic activity of the peptide; and
- b is a carboxy terminus or a substituent effective to facilitate coupling or to improve the immunogenic or antigenic activity of the peptide; or said peptide which contains deletions or conservative substitutions which do not alter the immunoreactivity of the peptide.

12. The mixture or combination according to claim 10 comprising at least the following peptides:

a-AIVSSPSHNSLILPPFSLSPVPTLGSR-b    (BCH-416)

a-PHSNLDHILEPSIPWKSKPYVEPTAPQVL-b    (BCH-234)

wherein
- a is an amino terminus or a substituent effective to facilitate coupling or to improve the immunogenic or antigenic activity of the peptide; and
- b is a carboxy terminus or a substituent effective to facilitate coupling or to improve the immunogenic or antigenic activity of the peptide; or said peptide which contains deletions or conservative substitutions which do not alter the immunoreactivity of the peptide.

13. The mixture or combination according to claim 10 comprising at least the following peptides:

a-AIVSSPSHNSLILPPFSLSPVPTLGSR-b    (SEQ ID NO:5) (BCH-416)

a-PHSNLDHILEPSIPWKSKPYVEPTAPQVL-b    (SEQ ID NO:15) (BCH-234)

a-TSEPTQPPPTSPPLLVHDSDLEHVL-b    (SEQ ID NO:12) (BCH-456)

wherein
- a is an amino terminus or a substituent effective to facilitate coupling or to improve the immunogenic or antigenic activity of the peptide; and
- b is a carboxy terminus or a substituent effective to facilitate coupling or to improve the immunogenic or antigenic activity of the peptide; or said peptide which contains deletions or conservative substitutions which do not alter the immunoreactivity of the peptide.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 488 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met  Gly  Lys  Phe  Leu  Ala  Thr  Leu  Ile  Leu  Phe  Phe  Gln  Phe  Cys  Pro
 1              5                        10                       15

Leu  Ile  Phe  Gly  Asp  Tyr  Ser  Pro  Ser  Cys  Cys  Thr  Leu  Thr  Ile  Gly
              20                        25                       30

Val  Ser  Ser  Tyr  His  Ser  Lys  Pro  Cys  Asn  Pro  Ala  Gln  Pro  Val  Cys
          35                        40                       45

Ser  Trp  Thr  Leu  Asp  Leu  Leu  Ala  Leu  Ser  Ala  Asp  Gln  Ala  Leu  Gln
     50                        55                       60

Pro  Pro  Cys  Pro  Asn  Leu  Val  Ser  Tyr  Ser  Tyr  His  Ala  Thr  Tyr
 65                       70                       75                       80

Ser  Leu  Tyr  Leu  Phe  Pro  His  Trp  Thr  Lys  Lys  Pro  Asn  Arg  Asn  Gly
                    85                        90                       95

Gly  Gly  Tyr  Tyr  Ser  Ala  Ser  Tyr  Ser  Asp  Pro  Cys  Ser  Leu  Lys  Cys
               100                       105                      110

Pro  Tyr  Leu  Gly  Cys  Gln  Ser  Trp  Thr  Cys  Pro  Tyr  Thr  Gly  Ala  Val
          115                       120                      125

Ser  Ser  Pro  Tyr  Trp  Lys  Phe  Gln  His  Asp  Val  Asn  Phe  Thr  Gln  Glu
     130                       135                      140

Val  Ser  Arg  Leu  Asn  Ile  Asn  Leu  His  Phe  Ser  Lys  Cys  Gly  Phe  Pro
145                       150                      155                      160

Phe  Ser  Leu  Leu  Val  Asp  Ala  Pro  Gly  Tyr  Asp  Pro  Ile  Trp  Phe  Leu
               165                       170                      175

Asn  Thr  Glu  Pro  Ser  Gln  Leu  Pro  Pro  Thr  Ala  Pro  Pro  Leu  Leu  Pro
               180                       185                      190

His  Ser  Asn  Leu  Asp  His  Ile  Leu  Glu  Pro  Ser  Ile  Pro  Trp  Lys  Ser
          195                       200                      205

Lys  Leu  Leu  Thr  Leu  Val  Gln  Leu  Thr  Leu  Gln  Ser  Thr  Asn  Tyr  Thr
     210                       215                      220

Cys  Ile  Val  Cys  Ile  Asp  Arg  Ala  Ser  Leu  Ser  Thr  Trp  His  Val  Leu
225                       230                      235                      240

Tyr  Ser  Pro  Asn  Val  Ser  Val  Pro  Ser  Ser  Ser  Thr  Pro  Leu  Leu
               245                       250                      255

Tyr  Pro  Ser  Leu  Ala  Leu  Pro  Ala  Pro  His  Leu  Thr  Leu  Pro  Phe  Asn
               260                       265                      270

Trp  Thr  His  Cys  Phe  Asp  Pro  Gln  Ile  Gln  Ala  Ile  Val  Ser  Ser  Pro
          275                       280                      285

Cys  His  Asn  Ser  Leu  Ile  Leu  Pro  Pro  Phe  Ser  Leu  Ser  Pro  Val  Pro
     290                       295                      300

Thr  Leu  Gly  Ser  Arg  Ser  Arg  Arg  Ala  Val  Pro  Val  Ala  Val  Trp  Leu
305                       310                      315                      320

Val  Ser  Ala  Leu  Ala  Met  Gly  Ala  Gly  Val  Ala  Gly  Gly  Ile  Thr  Gly
               325                       330                      335

Ser  Met  Ser  Leu  Ala  Ser  Gly  Lys  Ser  Leu  Leu  His  Glu  Val  Asp  Lys
               340                       345                      350

Asp  Ile  Ser  Gln  Leu  Thr  Gln  Ala  Ile  Val  Lys  Asn  His  Lys  Asn  Leu
          355                       360                      365

Leu  Lys  Ile  Ala  Gln  Tyr  Ala  Ala  Gln  Asn  Arg  Arg  Gly  Leu  Asp  Leu
     370                       375                      380

Leu  Phe  Trp  Glu  Gln  Gly  Gly  Leu  Cys  Lys  Ala  Leu  Gln  Glu  Gln  Cys
385                       390                      395                      400

Arg  Phe  Pro  Asn  Ile  Thr  Asn  Ser  His  Val  Pro  Ile  Leu  Gln  Glu  Arg
               405                       410                      415

Pro  Pro  Leu  Glu  Asn  Arg  Val  Leu  Thr  Gly  Trp  Gly  Leu  Asn  Trp  Asp
               420                       425                      430
```

-continued

| Leu | Gly | Leu | Ser | Gln | Trp | Ala | Arg | Glu | Ala | Leu | Gln | Thr | Gly | Ile | Thr |
|-----|-----|-----|-----|-----|-----|-----|-----|-----|-----|-----|-----|-----|-----|-----|-----|
|     |     | 435 |     |     |     | 440 |     |     |     |     | 445 |     |     |     |     |

| Leu | Val | Ala | Leu | Leu | Leu | Val | Ile | Leu | Ala | Gly | Pro | Cys | Ile | Leu |
|-----|-----|-----|-----|-----|-----|-----|-----|-----|-----|-----|-----|-----|-----|-----|
|     | 450 |     |     |     | 455 |     |     |     | 460 |     |     |     |     |     |

| Arg | Gln | Leu | Arg | His | Leu | Pro | Ser | Arg | Val | Arg | Tyr | Pro | His | Tyr | Ser |
|-----|-----|-----|-----|-----|-----|-----|-----|-----|-----|-----|-----|-----|-----|-----|-----|
| 465 |     |     |     |     | 470 |     |     |     |     | 475 |     |     |     |     | 480 |

| Leu | Ile | Lys | Pro | Glu | Ser | Ser | Leu |
|-----|-----|-----|-----|-----|-----|-----|-----|
|     |     |     |     | 485 |     |     |     |

( 2 ) INFORMATION FOR SEQ ID NO:2:

( i ) SEQUENCE CHARACTERISTICS:
        ( A ) LENGTH: 486 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Gly | Asn | Val | Phe | Phe | Leu | Leu | Leu | Phe | Ser | Leu | Thr | His | Phe | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Ala | Gln | Gln | Ser | Arg | Cys | Thr | Leu | Thr | Ile | Gly | Ile | Ser | Ser | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| His | Ser | Ser | Pro | Cys | Ser | Pro | Thr | Gln | Pro | Val | Cys | Thr | Trp | Asn | Leu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Asp | Leu | Asn | Ser | Leu | Thr | Thr | Asp | Gln | Arg | Leu | His | Pro | Pro | Cys | Pro |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Asn | Leu | Ile | Thr | Tyr | Ser | Gly | Phe | His | Lys | Thr | Tyr | Ser | Leu | Tyr | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Phe | Pro | His | Trp | Ile | Lys | Lys | Pro | Asn | Arg | Gln | Gly | Leu | Gly | Tyr | Tyr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ser | Pro | Ser | Tyr | Asn | Asp | Pro | Cys | Ser | Leu | Gln | Cys | Pro | Tyr | Leu | Gly |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| Cys | Gln | Ala | Trp | Thr | Ser | Ala | Tyr | Thr | Gly | Pro | Val | Ser | Ser | Pro | Ser |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Trp | Lys | Phe | His | Ser | Asp | Val | Asn | Phe | Thr | Gln | Glu | Val | Ser | Gln | Val |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ser | Leu | Arg | Leu | His | Phe | Ser | Lys | Cys | Gly | Ser | Ser | Met | Thr | Leu | Leu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Val | Asp | Ala | Pro | Gly | Tyr | Asp | Pro | Leu | Trp | Phe | Ile | Thr | Ser | Glu | Pro |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Thr | Gln | Pro | Pro | Pro | Thr | Ser | Pro | Pro | Leu | Val | His | Asp | Ser | Asp | Leu |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Glu | His | Val | Leu | Thr | Pro | Ser | Thr | Ser | Trp | Thr | Thr | Lys | Ile | Leu | Lys |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Phe | Ile | Gln | Leu | Thr | Leu | Gln | Ser | Thr | Asn | Tyr | Ser | Cys | Met | Val | Cys |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Val | Asp | Arg | Ser | Ser | Leu | Ser | Ser | Trp | His | Val | Leu | Tyr | Thr | Pro | Asn |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ile | Ser | Ile | Pro | Gln | Gln | Thr | Ser | Ser | Arg | Thr | Ile | Leu | Phe | Pro | Ser |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Leu | Ala | Leu | Pro | Ala | Pro | Ser | Gln | Pro | Phe | Pro | Trp | Thr | His | Cys |
|-----|-----|-----|-----|-----|-----|-----|-----|-----|-----|-----|-----|-----|-----|-----|
|     |     |     | 260 |     |     |     | 265 |     |     |     |     | 270 |     |     |

| Tyr | Gln | Pro | Arg | Leu | Gln | Ala | Ile | Thr | Thr | Asp | Asn | Cys | Asn | Asn | Ser |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Ile | Ile | Leu | Pro | Pro | Phe | Ser | Leu | Ala | Pro | Val | Pro | Pro | Pro | Ala | Thr |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

```
Arg  Arg  Arg  Arg  Ala  Val  Pro  Ile  Ala  Val  Trp  Leu  Val  Ser  Ala  Leu
305                      310                 315                           320

Ala  Ala  Gly  Thr  Gly  Ile  Ala  Gly  Gly  Val  Thr  Gly  Ser  Leu  Ser  Leu
                    325                      330                      335

Ala  Ser  Ser  Lys  Ser  Leu  Leu  Leu  Glu  Val  Asp  Lys  Asp  Ile  Ser  His
               340                 345                           350

Leu  Thr  Gln  Ala  Ile  Val  Lys  Asn  His  Gln  Asn  Ile  Leu  Arg  Val  Ala
          355                 360                      365

Gln  Tyr  Ala  Ala  Gln  Asn  Arg  Arg  Gly  Leu  Asp  Leu  Leu  Phe  Trp  Glu
     370                      375                 380

Gln  Gly  Gly  Leu  Cys  Lys  Ala  Ile  Gln  Glu  Gln  Cys  Cys  Phe  Leu  Asn
385                 390                      395                           400

Ile  Ser  Asn  Thr  His  Val  Ser  Val  Leu  Gln  Glu  Arg  Pro  Pro  Leu  Glu
                    405                      410                      415

Lys  Arg  Val  Ile  Thr  Gly  Trp  Gly  Leu  Asn  Trp  Asp  Leu  Gly  Leu  Ser
               420                      425                 430

Gln  Trp  Ala  Arg  Glu  Ala  Leu  Gln  Thr  Gly  Ile  Thr  Ile  Leu  Ala  Leu
          435                      440                 445

Leu  Leu  Leu  Val  Ile  Leu  Phe  Gly  Pro  Cys  Ile  Leu  Arg  Gln  Ile  Gln
     450                      455                 460

Ala  Leu  Pro  Gln  Arg  Leu  Gln  Asn  Arg  His  Asn  Gln  Tyr  Ser  Leu  Ile
465                      470                 475                           480

Asn  Pro  Glu  Thr  Met  Leu
                    485
```

( 2 ) INFORMATION FOR SEQ ID NO:3:

( i ) SEQUENCE CHARACTERISTICS:
        ( A ) LENGTH: 429 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met  Gly  Gln  Ile  Phe  Ser  Arg  Ser  Ala  Ser  Pro  Ile  Pro  Arg  Pro  Pro
1                   5                   10                       15

Arg  Gly  Leu  Ala  Ala  His  His  Trp  Leu  Asn  Phe  Leu  Gln  Ala  Ala  Tyr
               20                 25                      30

Arg  Leu  Glu  Pro  Gly  Pro  Ser  Ser  Tyr  Asp  Phe  His  Gln  Leu  Lys  Lys
          35                 40                      45

Phe  Leu  Lys  Ile  Ala  Leu  Glu  Thr  Pro  Ala  Arg  Ile  Cys  Pro  Ile  Asn
     50                 55                      60

Tyr  Ser  Leu  Leu  Ala  Ser  Leu  Leu  Pro  Lys  Gly  Tyr  Pro  Gly  Arg  Val
65                  70                      75                           80

Asn  Glu  Ile  Leu  His  Ile  Leu  Ile  Gln  Thr  Gln  Ala  Gln  Ile  Pro  Ser
               85                 90                      95

Arg  Pro  Ala  Pro  Pro  Pro  Ser  Ser  Pro  Thr  His  Asp  Pro  Pro  Asp  Asp
          100                105                     110

Ser  Asp  Pro  Gln  Ile  Pro  Pro  Tyr  Val  Glu  Pro  Thr  Ala  Pro  Gln  Gln
     115                120                     125

Val  Leu  Pro  Val  Met  His  Pro  His  Gly  Ala  Pro  Pro  Asn  His  Arg  Pro
     130                135                     140

Trp  Gln  Met  Lys  Asp  Leu  Gln  Ala  Ile  Lys  Gln  Glu  Val  Ser  Gln  Ala
145                 150                     155                          160

Ala  Pro  Gly  Ser  Pro  Gln  Phe  Met  Gln  Thr  Ile  Arg  Leu  Ala  Val  Gln
               165                170                     175
```

|   |   |   |   |   |   |   |   |   |   |   |   |   |   |   |
|---|---|---|---|---|---|---|---|---|---|---|---|---|---|---|
| Gln | Phe | Asp | Pro<br>180 | Thr | Ala | Lys | Asp<br>185 | Leu | Gln | Asp | Leu<br>190 | Leu | Gln | Tyr | Leu |
| Cys | Ser | Ser<br>195 | Leu | Val | Ala | Ser | Leu<br>200 | His | His | Gln | Gln<br>205 | Leu | Asp | Ser | Leu |
| Ile | Ser<br>210 | Glu | Ala | Glu | Thr | Arg<br>215 | Gly | Ile | Thr | Gly | Tyr<br>220 | Asn | Pro | Leu | Ala |
| Gly<br>225 | Pro | Leu | Arg | Val | Gln<br>230 | Ala | Asn | Asn | Pro | Gln<br>235 | Gln | Gly | Leu | Arg<br>240 |
| Arg | Glu | Tyr | Gln | Gln<br>245 | Leu | Trp | Leu | Ala | Ala<br>250 | Phe | Ala | Ala | Leu | Pro<br>255 | Gly |
| Ser | Ala | Lys | Asp<br>260 | Pro | Ser | Trp | Ala | Ser<br>265 | Ile | Leu | Gln | Gly | Leu<br>270 | Glu | Glu |
| Pro | Tyr | His<br>275 | Ala | Phe | Val | Glu | Arg<br>280 | Leu | Asn | Ile | Ala | Leu<br>285 | Asp | Asn | Gly |
| Leu | Pro<br>290 | Glu | Gly | Thr | Pro | Lys<br>295 | Asp | Pro | Ile | Leu | Arg<br>300 | Ser | Leu | Ala | Tyr |
| Ser | Asn<br>305 | Ala | Asn | Lys | Glu<br>310 | Cys | Gly | Lys | Leu | Leu<br>315 | Gln | Ala | Arg | Gly | His<br>320 |
| Thr | Asn | Ser | Pro | Leu<br>325 | Gly | Asp | Met | Leu | Arg<br>330 | Ala | Cys | Gln | Thr | Trp<br>335 | Thr |
| Pro | Lys | Asp | Lys<br>340 | Thr | Lys | Val | Leu | Val<br>345 | Val | Gln | Pro | Lys | Lys<br>350 | Pro | Pro |
| Pro | Asn | Gln<br>355 | Pro | Cys | Phe | Arg | Cys<br>360 | Gly | Lys | Ala | Gly | His<br>365 | Trp | Ser | Arg |
| Asp | Cys<br>370 | Thr | Gln | Pro | Arg | Pro<br>375 | Pro | Pro | Gly | Pro | Cys<br>380 | Pro | Leu | Cys | Gln |
| Asp<br>385 | Pro | Thr | His | Trp | Lys<br>390 | Arg | Asp | Cys | Pro | Arg<br>395 | Leu | Lys | Pro | Thr | Ile<br>400 |
| Pro | Glu | Pro | Glu | Pro<br>405 | Glu | Glu | Asp | Ala | Leu<br>410 | Leu | Leu | Asp | Leu<br>415 | Pro | Ala |
| Asp | Ile | Pro | His<br>420 | Pro | Lys | Asn | Ser | Ile<br>425 | Gly | Gly | Glu | Val |   |   |   |

( 2 ) INFORMATION FOR SEQ ID NO:4:

( i ) SEQUENCE CHARACTERISTICS:
        ( A ) LENGTH: 433 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

|   |   |   |   |   |   |   |   |   |   |   |   |   |   |   |
|---|---|---|---|---|---|---|---|---|---|---|---|---|---|---|
| Met<br>1 | Gly | Gln | Ile | His<br>5 | Gly | Leu | Ser | Pro | Thr<br>10 | Pro | Ile | Pro | Lys | Ala<br>15 | Pro |
| Arg | Gly | Leu | Ser<br>20 | Thr | His | His | Trp<br>25 | Leu | Asn | Phe | Leu | Gln<br>30 | Ala | Ala | Tyr |
| Arg | Leu | Gln<br>35 | Pro | Arg | Pro | Ser | Asp<br>40 | Phe | Asp | Phe | Gln | Gln<br>45 | Leu | Arg | Arg |
| Phe | Leu<br>50 | Lys | Leu | Ala | Leu | Lys<br>55 | Thr | Pro | Ile | Trp | Leu<br>60 | Asn | Pro | Ile | Asp |
| Tyr<br>65 | Ser | Leu | Leu | Ala | Ser<br>70 | Leu | Ile | Pro | Lys | Gly<br>75 | Tyr | Pro | Gly | Arg | Val<br>80 |
| Val | Glu | Ile | Ile | Asn<br>85 | Ile | Leu | Val | Lys | Asn<br>90 | Gln | Val | Ser | Pro<br>95 | Ser | Ala |
| Pro | Ala | Ala | Pro<br>100 | Val | Pro | Thr | Pro | Ile<br>105 | Cys | Pro | Thr | Thr | Thr<br>110 | Pro | Pro |
| Pro | Pro | Pro | Pro | Pro | Ser | Pro | Glu | Ala | His | Val | Pro | Pro | Pro | Tyr | Val |

|     |     |     |     |     | 115 |     |     |     |     | 120 |     |     |     |     | 125 |     |     |     |
|-----|-----|-----|-----|-----|-----|-----|-----|-----|-----|-----|-----|-----|-----|-----|-----|-----|-----|-----|

Glu Pro Thr Thr Thr Gln Cys Phe Pro Ile Leu His Pro Pro Gly Ala
    130             135                 140

Pro Ser Ala His Arg Pro Trp Gln Met Lys Asp Leu Gln Ala Ile Lys
145             150                 155                     160

Gln Glu Val Ser Ser Ser Ala Leu Gly Ser Pro Gln Phe Met Gln Thr
            165                 170                 175

Leu Arg Leu Ala Val Gln Gln Phe Asp Pro Thr Ala Lys Asp Leu Gln
            180             185                 190

Asp Leu Leu Gln Tyr Leu Cys Ser Ser Leu Val Val Ser Leu His His
        195             200                 205

Gln Gln Leu Asn Thr Leu Ile Thr Glu Ala Glu Thr Arg Gly Met Thr
210             215                 220

Gly Tyr Asn Pro Met Ala Gly Pro Leu Arg Met Gln Ala Asn Asn Pro
225             230             235                         240

Ala Gln Gln Gly Leu Arg Arg Glu Tyr Gln Asn Leu Trp Leu Ala Ala
            245             250                 255

Phe Ser Thr Leu Pro Gly Asn Thr Arg Asp Pro Ser Trp Ala Ala Ile
        260             265                 270

Leu Gln Gly Leu Glu Glu Pro Tyr Cys Ala Phe Val Glu Arg Leu Asn
        275             280             285

Val Ala Leu Asp Asn Gly Leu Pro Glu Gly Thr Pro Lys Glu Pro Ile
    290             295             300

Leu Arg Ser Leu Ala Tyr Ser Asn Ala Asn Lys Glu Cys Gln Lys Ile
305             310             315                     320

Leu Gln Ala Arg Gly His Thr Asn Ser Pro Leu Gly Glu Met Leu Arg
            325                 330             335

Thr Cys Gln Ala Trp Thr Pro Lys Asp Lys Thr Lys Val Leu Val Val
            340             345                 350

Gln Pro Arg Arg Pro Pro Pro Thr Gln Pro Cys Phe Arg Cys Gly Lys
        355             360             365

Val Gly His Trp Ser Arg Asp Cys Thr Gln Pro Arg Pro Pro Pro Gly
    370             375                 380

Pro Cys Pro Leu Cys Gln Asp Pro Ser His Trp Lys Arg Asp Cys Pro
385             390             395                     400

Gln Leu Lys Pro Pro Gln Glu Glu Gly Glu Pro Leu Leu Leu Asp Leu
            405             410                 415

Pro Ser Thr Ser Gly Thr Thr Glu Glu Lys Asn Ser Leu Arg Gly Glu
            420             425                 430

Ile ( 2 ) INFORMATION FOR SEQ ID NO:5:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Ala Ile Val Ser Ser Pro Ser His Asn Ser Leu Ile Leu Pro Pro Phe
1               5                   10                  15

Ser Leu Ser Pro Val Pro Thr Leu Gly Ser Arg
            20              25

( 2 ) INFORMATION FOR SEQ ID NO:6:

( i ) SEQUENCE CHARACTERISTICS:
  ( A ) LENGTH: 22 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:6:

```
Leu  Val  His  Asp  Ser  Asp  Leu  Glu  His  Val  Leu  Thr  Pro  Ser  Thr  Ser
1                 5                           10                          15

Trp  Thr  Thr  Lys  Ile  Leu
                20
```

( 2 ) INFORMATION FOR SEQ ID NO:7:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:7:

```
Thr  Thr  Asp  Asn  Ser  Asn  Asn  Ser  Ile  Ile  Leu  Pro  Pro  Phe  Ser  Leu
1                 5                           10                          15

Ala  Pro  Val
```

( 2 ) INFORMATION FOR SEQ ID NO:8:

( i ) SEQUENCE CHARACTERISTICS:
    ( A ) LENGTH: 27 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:8:

```
Tyr  Gln  Pro  Arg  Leu  Gln  Ala  Ile  Thr  Thr  Asp  Asn  Ser  Asn  Asn  Ser
1                 5                           10                          15

Ile  Ile  Leu  Pro  Pro  Phe  Ser  Leu  Ala  Pro  Val
                20                      25
```

( 2 ) INFORMATION FOR SEQ ID NO:9:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:9:

```
Thr  Thr  Asp  Asn  Ser  Asn  Asn  Ser  Ile  Ile  Leu  Pro  Pro  Phe  Ser  Leu
1                 5                           10                          15

Ala  Pro  Val  Pro  Pro  Pro  Ala  Thr  Arg
                20                      25
```

( 2 ) INFORMATION FOR SEQ ID NO:10:

( i ) SEQUENCE CHARACTERISTICS:
    ( A ) LENGTH: 31 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:10:

```
Phe  Ile  Thr  Ser  Glu  Pro  Thr  Gln  Pro  Pro  Pro  Thr  Ser  Pro  Pro  Leu
1                 5                           10                          15
```

```
       Val  His  Asp  Ser  Asp  Leu  Glu  His  Val  Leu  Thr  Pro  Ser  Thr  Ser
                 20                       25                       30
```

(2) INFORMATION FOR SEQ ID NO:11:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:11:

```
  Thr  Ser  Glu  Pro  Thr  Gln  Pro  Pro  Pro  Thr  Ser  Pro  Pro  Leu  Val  His
  1              5                        10                       15

Asp  Ser  Asp  Leu  Glu  His  Val  Leu
                 20
```

(2) INFORMATION FOR SEQ ID NO:12:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:12:

```
  Thr  Ser  Glu  Pro  Thr  Gln  Pro  Pro  Pro  Thr  Ser  Pro  Pro  Leu  Leu  Val
  1              5                        10                       15

His  Asp  Ser  Asp  Leu  Glu  His  Val  Leu
                 20                       25
```

(2) INFORMATION FOR SEQ ID NO:13:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:13:

```
  Gln  Gln  Gly  Leu  Arg  Arg  Glu  Tyr  Gln  Gln  Leu  Trp  Leu  Ala  Ala  Phe
  1              5                        10                       15

Ala  Ala  Leu  Pro  Gly  Ser
                 20
```

(2) INFORMATION FOR SEQ ID NO:14:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:14:

```
  Gln  Gln  Gly  Leu  Arg  Arg  Glu  Tyr  Gln  Asn  Leu  Trp  Leu  Ala  Ala  Phe
  1              5                        10                       15

Ser  Thr  Leu  Pro  Gly  Asn
                 20
```

(2) INFORMATION FOR SEQ ID NO:15:

(i) SEQUENCE CHARACTERISTICS:
        (A) LENGTH: 29 amino acids
        (B) TYPE: amino acid ( D ) TOPOLOGY: linear ( i i ) MOLECULE TYPE: peptide ( x i ) SEQUENCE DESCRIPTION: SEQ ID NO:15:

Pro His Ser Asn Leu Asp His Ile Leu Glu Pro Ser Ile Pro Trp Lys
1               5                   10                  15

Ser Lys Pro Tyr Val Glu Pro Thr Ala Pro Gln Val Leu
            20                  25

( 2 ) INFORMATION FOR SEQ ID NO:16:

( i ) SEQUENCE CHARACTERISTICS:
       ( A ) LENGTH: 18 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:16:

His Ser Asn Leu Asp His Ile Leu Glu Pro Ser Ile Pro Trp Lys Ser
1               5                   10                  15

Lys Leu ( 2 ) INFORMATION FOR SEQ ID NO:17:

( i ) SEQUENCE CHARACTERISTICS:
       ( A ) LENGTH: 11 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:17:

Pro Tyr Val Glu Pro Thr Ala Pro Gln Val Leu
1               5                   10

( 2 ) INFORMATION FOR SEQ ID NO:18:

( i ) SEQUENCE CHARACTERISTICS:
       ( A ) LENGTH: 33 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:18:

Tyr Gln Pro Arg Leu Gln Ala Ile Thr Thr Asp Asn Cys Asn Asn Ser
1               5                   10                  15

Ile Ile Leu Pro Pro Phe Ser Leu Ala Pro Val Pro Pro Pro Ala Thr
            20                  25                  30

Arg ( 2 ) INFORMATION FOR SEQ ID NO:19:

( i ) SEQUENCE CHARACTERISTICS:
       ( A ) LENGTH: 37 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:19:

Phe Ile Thr Ser Glu Pro Thr Gln Pro Pro Thr Ser Pro Pro Leu
1               5                   10                  15

Val His Asp Ser Asp Leu Glu His Val Leu Thr Pro Ser Thr Ser Trp
            20                  25                  30

-continued

```
Thr Thr Lys Ile Leu
        35
```

(2) INFORMATION FOR SEQ ID NO:20:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:20:

```
Pro Tyr Val Glu Pro Thr Thr Thr Gln Cys Phe
 1           5                   10
```